United States Patent
DiMagno

(10) Patent No.: US 9,594,088 B2
(45) Date of Patent: Mar. 14, 2017

(54) MULTIPLE TIME WINDOWS WITH ASSOCIATED CALIBRATION CURVES FOR EXTENDING THE RANGE OF AN ASSAY

(71) Applicant: Ortho-Clinical Diagnostics, Inc., Raritan, NJ (US)

(72) Inventor: Theodore J. DiMagno, Penfield, NY (US)

(73) Assignee: Orth-Clinical Diagnostics, Inc., Raritan, NJ (US)

(*) Notice: Subject to any disclaimer, the term of this patent is extended or adjusted under 35 U.S.C. 154(b) by 1016 days.

(21) Appl. No.: 13/758,562

(22) Filed: Feb. 4, 2013

(65) Prior Publication Data
US 2013/0203174 A1    Aug. 8, 2013

Related U.S. Application Data

(60) Provisional application No. 61/595,408, filed on Feb. 6, 2012.

(51) Int. Cl.
*G01N 35/00* (2006.01)

(52) U.S. Cl.
CPC ... *G01N 35/0092* (2013.01); *G01N 35/00693* (2013.01); *Y10T 436/115831* (2015.01)

(58) Field of Classification Search
CPC ......... G01N 35/00693; G01N 35/0092; G01N 35/00; Y10T 436/115831; G06F 19/00; G06G 7/48
USPC ...... 422/50, 63–67; 436/43–47, 50, 55, 164, 436/166, 169, 171–172; 702/19, 22, 23, 702/25
See application file for complete search history.

(56) References Cited

U.S. PATENT DOCUMENTS

| | | | | |
|---|---|---|---|---|
| 3,742,196 A | * | 6/1973 | Durkos | G01N 35/025 250/565 |
| 3,886,045 A | * | 5/1975 | Meiattini | C12Q 1/28 435/14 |

(Continued)

FOREIGN PATENT DOCUMENTS

| | | |
|---|---|---|
| JP | 8-313533 | 11/1996 |
| JP | 9-189695 | 7/1997 |

(Continued)

OTHER PUBLICATIONS

Weller, M. G. et al, Mikrochimica Acta 1992, 108, 29-40.*

(Continued)

*Primary Examiner* — Arlen Soderquist
(74) *Attorney, Agent, or Firm* — Barclay Damon, LLP

(57) ABSTRACT

Disclosed is a use of reaction kinetics to generate multiple dose-response curves from a single reaction, thus eliminating the need to run a second experiment with additional sample, reagents, and time to cover a broader measuring range than is available in a standard assay. Using a single protocol, the differences in the reaction kinetics for different sample concentrations yield different responses at different measurement times. Selection of the appropriate dose-response curve cross-section increases the measuring range and accuracy of the assay from a single reaction without substantially increasing imprecision. Several overlapping dose-response curves are pieced together to provide a standard curve to ensure continuity throughout the expanded measuring range.

16 Claims, 20 Drawing Sheets

(56) References Cited

U.S. PATENT DOCUMENTS

| | | | | |
|---|---|---|---|---|
| 3,971,630 | A * | 7/1976 | Sandrock | G01N 21/253 356/409 |
| 4,029,401 | A * | 6/1977 | Nather | G01T 1/2045 250/328 |
| 4,135,883 | A * | 1/1979 | McNeil | G01N 21/07 422/413 |
| 4,160,818 | A * | 7/1979 | Smith | G01N 33/9473 436/536 |
| 4,231,750 | A * | 11/1980 | Dowben | G01N 33/542 250/302 |
| 4,234,538 | A * | 11/1980 | Ginsberg | G01N 21/253 250/226 |
| 4,236,894 | A * | 12/1980 | Sommervold | G01D 1/16 422/67 |
| 4,425,427 | A * | 1/1984 | Luderer | C12Q 1/54 422/412 |
| 4,430,299 | A * | 2/1984 | Horne | G01N 21/253 356/246 |
| 4,446,106 | A * | 5/1984 | Nelson | G01N 21/07 250/214 R |
| 4,515,889 | A * | 5/1985 | Klose | B01F 5/064 422/548 |
| 4,528,159 | A * | 7/1985 | Liston | B01L 3/505 356/244 |
| 4,595,661 | A | 6/1986 | Cragle et al. | |
| 4,968,148 | A * | 11/1990 | Chow | G01N 21/253 356/427 |
| 5,073,484 | A | 12/1991 | Swanson et al. | |
| 5,397,711 | A * | 3/1995 | Finckh | B01L 3/00 422/420 |
| 5,420,042 | A * | 5/1995 | Schafer | G01N 33/54313 436/164 |
| 5,565,364 | A * | 10/1996 | Schaefer | G01N 21/75 436/161 |
| 5,585,241 | A | 12/1996 | Lindmo | |
| 5,590,052 | A * | 12/1996 | Kopf-Sill | G01N 21/253 356/39 |
| 5,595,708 | A * | 1/1997 | Berndt | G01N 21/253 356/337 |
| 5,597,532 | A * | 1/1997 | Connolly | B01L 3/545 422/401 |
| 5,631,127 | A * | 5/1997 | Sundrehagen | G01N 33/68 435/15 |
| 5,646,046 | A * | 7/1997 | Fischer | G01N 33/4905 422/63 |
| 5,646,049 | A * | 7/1997 | Tayi | B01F 11/0022 422/63 |
| 5,766,875 | A * | 6/1998 | Hafeman | G01N 33/5008 356/4.01 |
| 5,789,262 | A * | 8/1998 | Tuengler | G01N 33/536 422/73 |
| 5,885,839 | A * | 3/1999 | Lingane | G01N 21/8483 436/169 |
| 5,928,532 | A * | 7/1999 | Koshimizu | G01N 21/68 156/345.25 |
| 5,948,368 | A | 9/1999 | Hirai et al. | |
| 6,044,330 | A * | 3/2000 | Patzke | G01N 33/557 356/341 |
| 6,108,607 | A | 8/2000 | Kono et al. | |
| 6,232,608 | B1 * | 5/2001 | Giebeler | G01N 21/6452 250/458.1 |
| 6,248,597 | B1 | 6/2001 | Eda et al. | |
| 7,054,759 | B2 | 5/2006 | Fukunaga et al. | |
| 7,067,791 | B2 * | 6/2006 | Sagatelyan | G01J 1/42 250/214 R |
| 7,118,916 | B2 * | 10/2006 | Matzinger | C12Q 1/00 422/105 |
| 7,226,777 | B2 * | 6/2007 | Kawamura | G01N 33/557 356/300 |
| 7,604,593 | B2 * | 10/2009 | Parris | A61B 5/14532 435/14 |
| 7,829,347 | B2 | 11/2010 | Song | |
| 7,856,325 | B2 * | 12/2010 | Ward | G06K 9/0053 435/91.2 |
| 8,560,251 | B2 * | 10/2013 | Mansouri | G01N 33/48792 435/14 |
| 9,121,827 | B2 * | 9/2015 | Mayer | G01N 21/6408 |
| 2003/0232321 | A1 * | 12/2003 | Lin | C12Q 1/54 435/4 |
| 2004/0078149 | A1 * | 4/2004 | Matzinger | C12Q 1/00 702/22 |
| 2005/0009102 | A1 * | 1/2005 | Kawamura | G01N 33/557 435/7.1 |
| 2005/0130249 | A1 * | 6/2005 | Parris | A61B 5/14532 435/14 |
| 2006/0252110 | A1 * | 11/2006 | Gregory | C12Q 1/26 435/25 |
| 2007/0259450 | A1 | 11/2007 | Bodenbach et al. | |
| 2008/0015836 | A1 * | 1/2008 | Ward | G06K 9/0053 703/11 |
| 2009/0308183 | A1 * | 12/2009 | Cohen | G01N 35/0092 73/864.21 |
| 2011/0207229 | A1 * | 8/2011 | Evers | B82Y 25/00 436/34 |
| 2013/0005046 | A1 * | 1/2013 | Mayer | G01N 21/6408 436/136 |
| 2013/0046478 | A1 * | 2/2013 | Mansouri | G01N 33/48792 702/19 |

FOREIGN PATENT DOCUMENTS

| | | |
|---|---|---|
| JP | 10-105545 | 4/1998 |
| JP | 2005-510706 | 4/2005 |
| JP | 2010-002398 | 1/2010 |
| WO | WO 94/03632 * | 2/1994 |
| WO | WO 03/046514 A2 | 6/2003 |
| WO | WO 2010/120917 A2 | 10/2010 |
| WO | WO 2011/109379 A1 | 9/2011 |

OTHER PUBLICATIONS

Reutens, Anne. T. et al, Journal of Clinical Endocrinology & Metabolism 1995, 80, 480-485.*

Valanne, A. et al, Journal of Virological Methods 2005, 129, 83-90.*

Japanese Office Action for JP 2013-020234; Dated: Aug. 9, 2016; 2 pages.

* cited by examiner

MULTIPLE TIME WINDOWS WITH ASSOCIATED CALIBRATION CURVES FOR EXTENDING THE RANGE OF AN ASSAY

BACKGROUND

A substance of interest, also termed an analyte, may be measured directly or, as is more often the case, indirectly. For indirect measurements a more readily detectable substance is formed by reacting the substance of interest with one or more reagents. The level of the more readily detectable substance is measured at a defined time after the initiation of the reaction. This level is converted into the level of the substance of interest by way of a calibration curve.

Calibration is a basic requirement for quantitative estimation of an analyte or substance—whether for dispensing or measurement. This generates a composite calibration curve to reduce errors. For instance, a clinical diagnostic analyzer or a point of care instrument measures analytes with the aid of a calibration curve—which curve is sometimes also referred to as a dose-response curve.

A clinical diagnostic analyzer is a complex machine with that is capable of both high accuracy and throughput. It is typically operated using software routines to both process samples and to detect errors in such processing or other errors—for instance in the samples being analyzed or a failure in its subsystems. FIG. 1 shows a clinical diagnostic analyzer 100 with four major component sub-systems or parts. It has a Reagent Management Center 110, a Sample Handling Center 120, a Supply Center 130 and a Processing Center 140. These subsystems are typically coordinated by a Scheduler—typically implemented with the aid of software—that specifies the particular operations to be performed by the clinical diagnostic analyzer subsystems on particular samples or reagents at specified time points. To aid in this task, the clinical diagnostic analyzer relies on a clock signal.

Analyte concentrations in a sample can typically be quantitatively detected by reading a signal during a short time window, for instance, in the clinical diagnostic analyzer of FIG. 1, in the Processing Center 140. Then, the detected signal strength is converted to analyte concentration. This conversion typically uses a single calibration curve. The time window may be short with tight tolerances for greater accuracy or with more forgiving specifications if the resultant errors are acceptable.

As is known in the prior art, a calibration curve is prepared using known analyte concentrations, and interpolation—and limited extrapolation—to allow calculation of analyte concentrations for substantially all signal strengths in the measurement range. Extending the range of measurements for analytes of interest has been a longstanding challenge. For instance, US Patent Publication No. 2007/0259450 describes a method for improving the range of an analyte test using special reagents. Another method for extending the range of measurements is provided by U.S. Pat. No. 7,829,347, which describes a method for detecting a region where the hook effect may be encountered to allow implementation of corrective measures. Similarly, U.S. Pat. No. 7,054,759 describes an algorithm using multiple calibration curves to counter the 'prozone phenomenon' or the 'prozone-like phenomenon', which is encountered when increasing the analyte level does not result in an increase in an absorbance signal, but instead even leads to a decrease in the absorbance signal.

The accuracy of a calibration curve may vary with the signal strength. Thus, measured analyte concentrations may have different errors in different parts of the calibration curve. In particular, on one hand, towards the lower end, i.e., with regard to the lower analyte detection limit, the measuring accuracy is limited by the low signal strength due to, for instance, the affinity and selectivity of the binding partners (often antibodies) or the extent to which a reaction has progressed. Further limits are placed by the detection optics' sensitivity at the low end which may be limited by the labels used, as is seen in the detection of amplification products based on the Polymerase Chain Reaction (PCR). On the other hand, saturation effects limit the measurements towards the upper end, i.e., corresponding to high analyte concentrations. Thus, in the case of high concentrations or levels of an analyte in the sample flattening due to saturation or exhaustion of a reagent limits the accuracy of detection. For consistently accurate measurements using a calibration curve, the curve should be substantially linear relative to the analyte concentration over broad ranges of analyte concentrations. In other words the measured analyte concentration should be directly proportional to the corresponding signal strength, which also makes the curves intuitive.

This is not always possible or practical. Still, there have been many attempts at making calibration curves more useful and intuitive. The signal strength may be mathematically transformed to generate a linear relationship, for instance by using the logarithm of the signal (or analyte concentration) to span a large range. However, this is not useful for all tests of interest.

There have been many attempts to make the calibration curve more useful in various assays. An assay is a procedure to detect an analyte using techniques that include optical, immunological, affinity, amplification, activity and the like to generate a signal. Some example assays use more than one technique such as PCR based detection of very small amounts of nucleic acid material. An example of improving calibration curves used in assays is disclosed by U.S. Pat. No. 6,248,597, which describes a heterogeneous agglutination immunoassay based on light scattering in which the dynamic measuring range is extended by particles differing in their light scattering properties. Binding partners having a high affinity for the analyte are immobilized on the particles which cause a large light scattering. In contrast, binding partners having a low affinity for the analyte are immobilized on the particles which exhibit low light scattering. This technique makes detection at low levels more sensitive while staving off saturation at high levels.

Another method is disclosed by U.S. Pat. No. 5,585,241. In order to increase the dynamic measuring range, it proposes in connection with a flow cytometry immunoassay that two particles of different sizes are loaded with two antibodies having different affinities for the same antigen (small particles loaded with high-affinity antibody, large particles loaded with low-affinity antibody).

A similar strategy is disclosed by U.S. Pat. No. 4,595,661, which uses a double standard curve, one from each particle type. Thus, the measurement of the sum of the contributions from the two binding reactions taking place in a mixed system. The low affinity antibody makes a significant contribution at high ligand concentrations while high sensitivity continues to be provided by the high-affinity antibody at low concentrations of the analyte. Each sample measurement therefore results in two measurement values—one for each particle size—and the two values must fit as a pair to the double standard curve for the analyte concentration in question.

U.S. Pat. No. 5,073,484 discloses that an immunologically detectable analyte can be quantitatively detected using several discrete, successive binding zones in a flow-through system. The number of zones in which the specific binding and detection reactions take place increases with an increasing amount of analyte in the sample. The number of zones in which analyte generates a signal correlates with the amount of analyte in the sample. Further, the number of binding zones can be increased in order to extend the measuring range. A disadvantage of this is that an automatic evaluation of the binding zones requires a complicated optical system which is able under certain circumstances to simultaneously detect and evaluate a large number of zones in order to thus allow a quantitative analyte determination.

Diagnostic instruments typically use a calibration curve based on a set of instrument responses to known sample values and fit to conform to a mathematical relationship—such as linear, quadratic, exponential, logarithmic and the like. This calibration curve, also known as a dose-response curve, is then read to determine values corresponding to an unknown sample. This curve allows instrument responses to unknown sample to be combined with the calibration curve to generate a value for the unknown sample.

The calibration curve itself often limits the useful measuring range of a test. This follows from the calibration curve shape, which while desired to be linear with an appreciable slope, is often inconveniently non-linear or too flat to provide adequate discrimination. Test values in such regions are difficult to pin down since small differences in sample strength may result in large changes in signal strength or large changes in sample strength correspond to even no appreciable change in signal strength. For example with diagnostic tests, these variables drive the performance of the test by relating predicted concentrations to well known performance characteristics such as linearity and limit of quantitation (see CLSI Guidelines EP6-A and EP17-A). The limitation in test performance can be limited by both (i) the actual flattening of response versus concentration below an acceptable threshold limit where no mathematical modeling can be helpful, and (ii) the failure of the mathematical model to adequately fit the actual response data.

An example of the difficulties due to flattening of response versus concentration is shown in FIG. 2. In this example, the dose-response curve is relatively flat between 0-0.5 au and between 3.2-6 au. The essential useful measuring range of the response function is between 0.5-3.2 au (between the broken lines), independent of the mathematical model used to fit the response data. Beyond this range, the flatness of the curve causes a poor correlation between response and concentration due to the imprecision of the measured response.

An example of a failure of the mathematical model to adequately fit the actual response data is shown in FIG. 3. In this example, the fitted calibration curve using a Logit/Log 4 function (broken line) does not fit the actual calibrator response data (inversely proportional dose-response curve). There is a small fitting deviation at low concentration where the fitted calibration curve flattens out the response. At high concentrations, there is a significant deviation between the fitted calibration curve and the calibration response data due to the flattening of the calibration curve at concentration greater than 1.5 au. Because of the lack of mathematical fit, the useful measuring range would be much smaller than the 0.02-2.7 range the calibrator response curve shape data suggests. In this example, the useful measuring range would be reduced to approximately 0.15-0.75 au (between the vertical broken lines) due to the lack of fit of the calibration model at both the low and high concentration regions.

In cases when the useful measuring range is limited by the calibration curve or fitting model, one would like to be able to generate useful dose-response curves that span greater than the approximate 0.5-3.2 au measuring range shown in FIG. 2. Expanding the measuring range without the having to run a second experiment—that uses additional reagents and sample—remains an unmet need.

SUMMARY

This disclosure utilizes the properties of the chemistry reaction kinetics to generate multiple dose-response curves from a single reaction, thus eliminating the need to run additional experiments to cover a broader measuring range than that available in a standard assay. Since within the same protocol (same sample volume, reagent volumes, incubation times, etc. . . . ) the differences in the reaction kinetics for different concentration samples can yield different responses at each different measurement time and with different accuracies or resolution, multiple experiments compromise accuracy and resolution of an assay.

The dose-response curve shown in FIG. 2 is a cross-section of these kinetic curves at a fixed time point after the reaction was initiated. Selection of the cross-section at a different reaction time will yield a dose-response curve with a different shape.

In the disclosed method and system, the measurement time windows, each also termed 'a time point', are selected such that with dose-response curves generated for each such time window, the measuring range of the assay from a single reaction is increased when these multiple calibration curves (dose-response curves) are used together. Preferably, the dose-response curves overlap.

A feature of this method and system is that it eliminates the need for running additional reactions (like in the VITROS™ Opiate High/Opiate Low assays) to increase the assay measuring range. The automation of clinical diagnostic analyzers and other testing platforms allows automatic selection of the appropriate calibration curve based on the magnitude of the signal in one of the measurement time windows. Thus, in the first measurement time window, the signal strength indicates whether the corresponding calibration curve should be used, or, the signal be measured at a later measurement time window. Notably, the measurement is from the same reaction mix, just at a later time. The signal is detected again at the later time period after the reaction has progressed further and interpreted based on the corresponding calibration curve, which provides acceptable resolution and accuracy. In this manner multiple calibration curves, each corresponding to a particular time point or window for measuring the signal, can be combined and accessed using decision rules driven by the signal strength at different specified time points/windows. Preferably, the different calibration curves partially overlap to ensure continuity throughout the expanded measuring range by ensuring that there is at least one test sample that is common to both the curves. In other words, a signal corresponding to the test sample in the overlapping portion is measured at two or more different time points. In some embodiments the overlap may be accomplished by extrapolation from adjacent calibration or dose-response curves. This is not the preferred embodiment of this disclosure. Further, because the multiple dose-response curves used are based on single reaction, the effective response magnitude that can be measured also increases, which results in improved assay precision.

In a preferred method for scheduling a test for measuring an analyte in a clinical analyzer supporting an extended range, the method comprises the steps of initiating the test using a reaction mix with a first signal strength read from the reaction mix at about a first predefined time point after initiating the test. This signal strength is used to determine if there is a corresponding acceptable calibration curve. Typically, the corresponding calibration curve is used to determine the analyte concentration or level with acceptable accuracy. If there is no corresponding calibration curve or if another determination of the analyte concentration or level is desired, then the signal strength is read from the reaction mix at a second later time point—in effect following a longer incubation. This signal strength may also be used to identify its corresponding calibration curve. The analyte level is determined from the appropriate calibration curve.

In some embodiments, analyte concentration or level is determined from the very first suitable calibration curve. In other embodiments, such a determination may be made using multiple acceptable calibration curves with averaging to get a single value for the analyte concentration or level.

A clinical analyzer supporting an extended range permits reading of the signal strength at a different time from the same reaction mix in addition to implementing a decision-making logic to direct the reading of the signal strengths at different times. In a preferred embodiment, the scheduler of the clinical analyzer allows dynamically scheduling a subsequent reading of the signal strength at a later time depending on the signal strength at an earlier time point. Thus, the first measurement of the signal strength helps determine if a measurement at a second time-point is required. If the signal strength measurement is required at a later time-point, resources are allocated for such a measurement. Of course, if the signal strength is adequate, then there may be no need to perform a second measurement of the signal strength after a longer incubation. On the other hand, if the signal strength is too low (or too high) to accurately measure the analyte concentration/level, then a longer incubation allows an improvement in the accuracy of the measurement. Such a read event is then programmed and provided for by the clinical analyzer supporting an extended range. Naturally, allocation of resources may require delaying some samples in the queue, or for the scheduler in the clinical analyzer to take other actions such as schedule the read event when resources are next available and the like. In some embodiments, the need for such a read event may result in arresting/stopping the reaction at a specified time point if the detector is not available.

A method or a clinical analyzer supporting an extended range includes a module or step for determining whether there is a suitable corresponding first calibration curve. In the absence of a suitable first calibration curve, a second time point for determining a second signal strength from the reaction mix is scheduled. Next, the second signal strength is determined at about the second time point followed by the identification of a second calibration curve corresponding to the second signal strength. Finally, the level of an analyte from one or more of the first signal strength and second signal strength is determined.

In the disclosed method for extending the range of an instrument for measuring an initial analyte level based on a time-variant signal, the signal reflecting an analyte level is measured at a specified time. The method comprises measuring a signal and determining if there is available a suitable calibration curve based on the signal strength. A first calibration curve at a first time point is used to estimate the initial analyte level if a signal strength corresponds to a predefined signal level for the first time point. A predefined signal level is preferably a threshold signal level. A condition based on the predefined signal level may specify that it needs to be met, or not met, or be exceeded and the like in order to use a particular calibration curve. A second calibration curve at a second time point is used to estimate the initial analyte level if the signal strength corresponds to a predefined signal level for the second time point and so on.

In the method and apparatus for measuring a level of an analyte using a plurality of calibration curves, each calibration curve is associated with at least one threshold signal level at each time point/window for identifying if the calibration curve is appropriate.

If a first condition, based on a first threshold, the first predetermined threshold associated with a first calibration curve from the plurality of calibration curves, is satisfied then the first calibration curve is used to generate a first measured value for the level of the analyte. As an example, the condition for using the first calibration curve may be set as a signal strength greater than the first predetermined threshold. If the signal strength is greater than the first predetermined threshold, then the first calibration curve is used to generate the first measured value for the concentration or level of the analyte.

Further, if a second condition based on a second threshold, the second threshold associated with a second calibration curve from the plurality of calibration curves, is satisfied then the second calibration curve is not used to measure the level of the analyte. As an example, the condition for not using the second calibration curve may be set as a signal strength less than the second threshold. If the signal strength is less than the second threshold, then the second calibration curve is not used to generate the measured value for the concentration or level of the analyte.

In another aspect, if more than one calibration curve from the plurality of calibration curves is available for measuring the level of the analyte, due to conditions corresponding to each of the more than one calibration curves being satisfied, then the measured level of the analyte is the mean of the analyte levels corresponding to each of the available calibration curves. This mean may be a weighted mean.

The thresholds may be set up such that the signal level satisfies one or more conditions selected from the group consisting of greater than, less than or equal to the threshold in order for the corresponding calibration curve to be used or a measurement made in the corresponding time window.

These and other features in some preferred exemplary embodiments are described below in detail with the aid of illustrative figures, which are briefly described next.

DETAILED DESCRIPTION

When measuring an analyte, one obtains a signal from a reaction mix incubated for a predefined time. This signal, measured during a specified time window, is converted into the level or concentration of the analyte using a calibration curve. Instead of using a physical curve, many implementations provide parameters defining the calibration curve—such as the slope and intercept of a line together with the range over which such parameters should be relied upon. One approach for accurately estimating the analyte is to use a linear calibration curve or a piecewise linear calibration curve. However, many regions of the calibration curve are still not suitable for inferring the analyte concentration with sufficient accuracy. As a result a range of measurements possible on an instrument is defined by the accuracy with which a measurement can be made using its calibration curve.

Varying the sample concentration, for instance by diluting it, may allow readings to be obtained that are within the range of the instrument. However, this requires carrying out another reaction with measurements associated with it.

This disclosure of techniques for extending the range of an instrument without requiring another reaction by employing two or more calibration curves also includes a procedure to dynamically select the appropriate calibration curve.

This limited measuring range is typically due to the shape of the response function, or due to the lack of fit of the calibration model, or due to another restrictive means. The end result is that the possible measuring range is limited unless another reaction is carried out with some varied parameters to change the characteristic response shape to allow measurement over a different range in the customary time window. The current disclosure provides two or more response curves from a single reaction to expand the possible range of measurements. This is accomplished by making measurements from a single reaction in two or more time windows.

Figure 4:
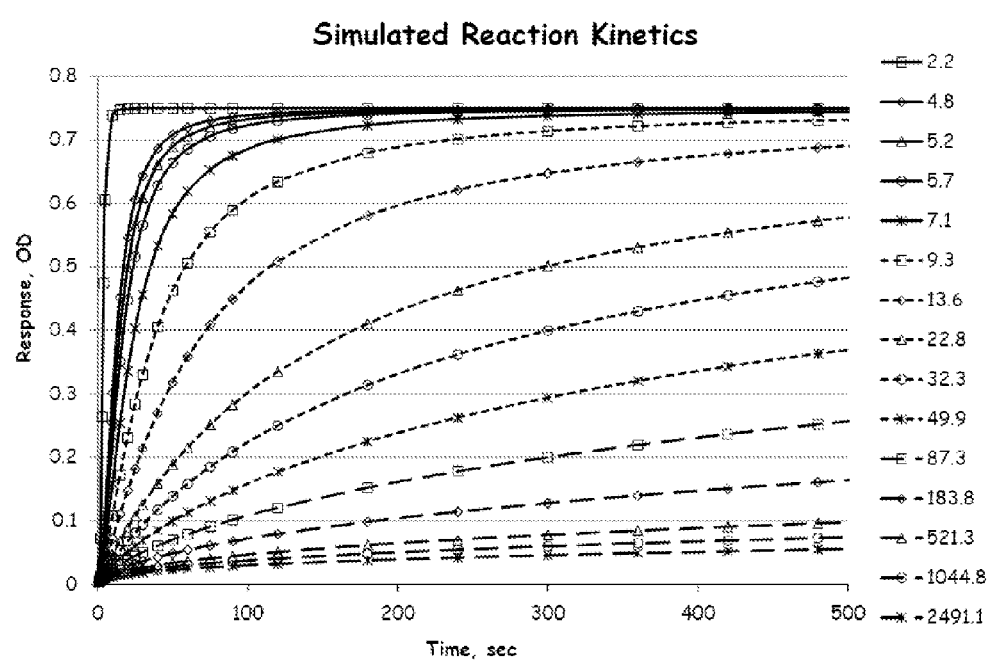
FIG. 4 shows a family of dose-response curves differentiated by the value of one of the Logit/Logit4 parameters.

The disclosed model concept is described using simulated reaction kinetics (Table 1, FIG. 4). Simulated reaction kinetics are assumed to be fit by the four parameter Logit/Log 4 model in accordance with Equation 1, where R is the response, C is the concentration, and $\beta_0$-$\beta_3$ are the four Logit/Log 4 parameters. It should be noted that alternative mathematical models could be used instead of the Logit/Log 4 method with no loss of generality.

$$R = \beta_0 + \frac{\beta_1}{1 + \exp^{-(\beta_2 + \beta_3 X ln C)}} \qquad \text{Equation 1}$$

In practice, the mathematical curve fitting model selected does not detract from the teachings of the disclosure. In the simulation shown in FIG. 4, $\beta_0$-$\beta_2$ are kept constant while $\beta_3$ is varied to yield a family of simulated kinetic curves—as is shown in the legend for FIG. 4. A family of analyte-concentration/instrument-signal curves (also known as "calibration curves" or dose-response curves) from the simulated kinetics are shown in FIG. 4 with the analyte concentration corresponding to the different $\beta_3$ values shown as parameters on the right.

Figure 5:
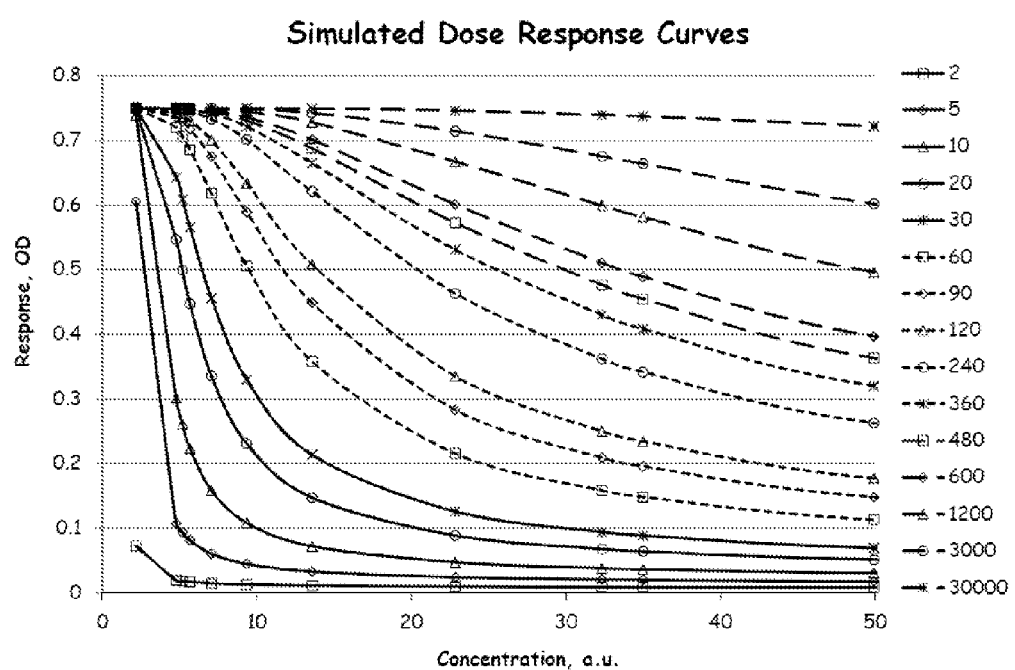
FIG. 5 shows a family of dose-response curves with the time at which the reaction results are read level as the parameter.

The curves in FIG. 5 were generated using Eq. 1 where the time for which the reaction is carried out is the parameter defining a series of plots between the observed signal on the y-axis and the initial analyte concentration along the x-axis. In FIG. 5 the time post-reaction for which the calibration curve was generated is shown in the Figure legend for each curve.

Figure 5B:
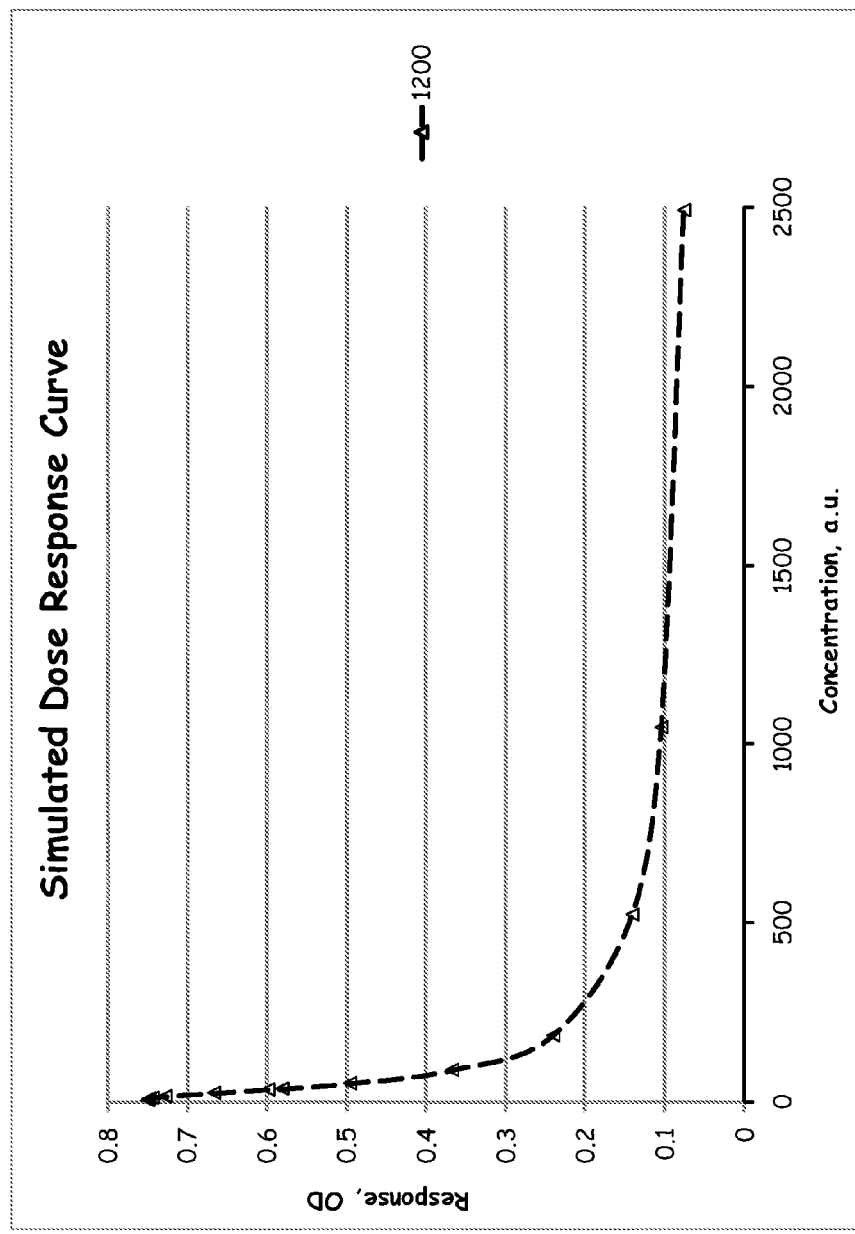
FIG. 5B shows the dose-response curve from FIG. 5 corresponding to 1200 seconds and covering a wider range of analyte levels.
Figure 6:
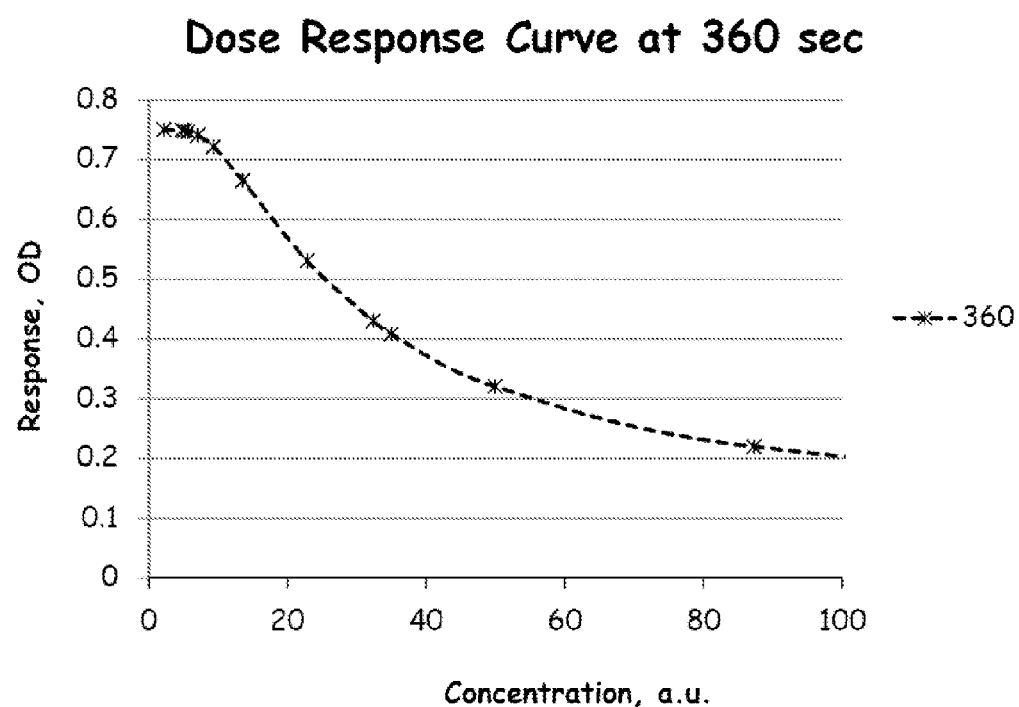
FIG. 6 shows a dose-response curve corresponding to FIG. 4 with time for reading the reaction results of 360 seconds scaled for relatively low levels of the analyte.
Figure 7:
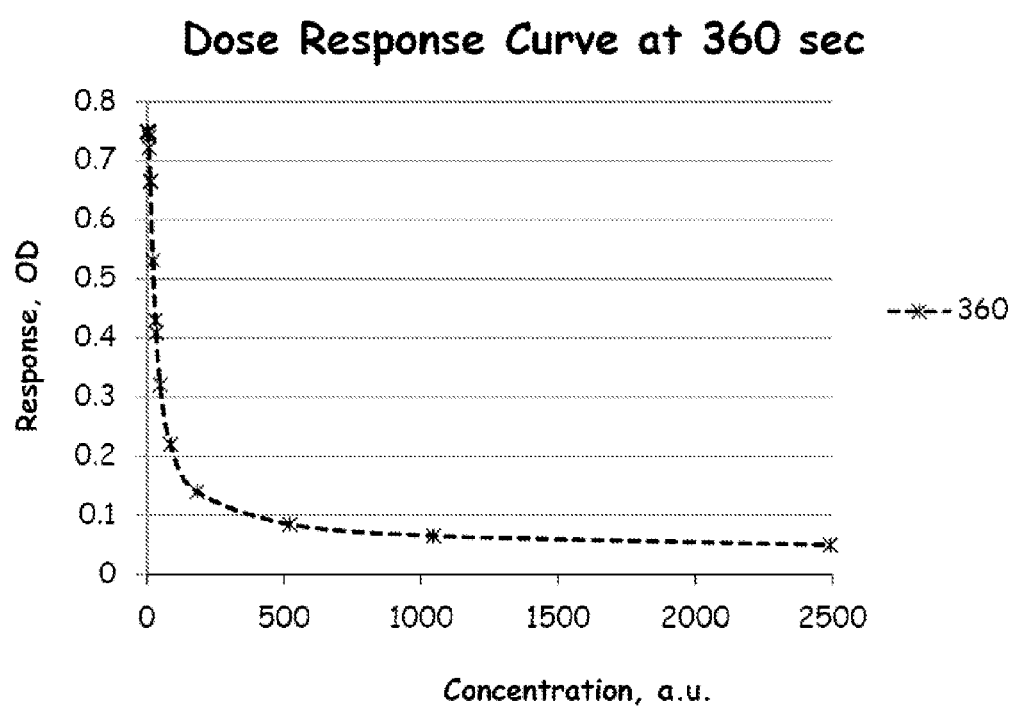
FIG. 7 shows a dose-response curve corresponding to FIG. 4 with time for reading the reaction results of 360 seconds scaled for relatively high levels of the analyte.

For instance, the kinetic curve in FIG. 5 corresponding to measurements made at 360 seconds after the initiation of the reaction show that there is seen a fairly flat response for all concentrations below 7 au (concentrations are shown on along the horizontal axis). This curve is reproduced in FIG. 6, which shows a flat response above 500 au as is illustrated in FIG. 7 for measurements made at 360 seconds after the initiation of a reaction. Because of the inherent shape of the calibration curve, the measuring range would be limited to approximately 10-500 au if a measurement window at 360 seconds was used with a single reaction mix. Earlier measurements would allow more accurate measurements at the lower end, but would not be suitable for higher analyte levels. For instance, a measurement range of ~2-50 au is possible from a single reaction mix if the measurements are made during a time window that corresponds to 20 seconds post initiation of the reaction. Similarly, a late measurement would be better suited to detect higher analyte concentrations, but at the cost of accuracy in detecting relatively lower analyte concentrations. As is readily seen in FIG. 5 and FIG. 5B, for an exemplary time window corresponding to 1200 seconds post initiation of the reaction, the measurement range is ~15-greater than 1000 au. At less than 15 au, the 1200 second curve is too flat as is illustrated in FIG. 5. Thus, no single calibration curve spans the entire measuring range between 2-2500 au using a single reaction mix. Customarily this limitation requires that multiple reactions be set up with different concentrations of reagents or test substances—even a dilution series to make accurate measurements.

TABLE 1

Logit/Log4 Parameters for the Simulated Reaction Kinetics

| $\beta_0$ | $\beta_1$ | $\beta_2$ | $\beta_3$ | Conc. Arbitrary units (au) |
|---|---|---|---|---|
| 0 | 0.75 | −5 | 4 | 2.19 |
| 0 | 0.75 | −5 | 2 | 4.78 |
| 0 | 0.75 | −5 | 1.9 | 5.19 |
| 0 | 0.75 | −5 | 1.8 | 5.69 |
| 0 | 0.75 | −5 | 1.6 | 7.06 |
| 0 | 0.75 | −5 | 1.4 | 9.34 |
| 0 | 0.75 | −5 | 1.2 | 13.56 |
| 0 | 0.75 | −5 | 1 | 22.83 |
| 0 | 0.75 | −5 | 0.9 | 32.32 |
| 0 | 0.75 | −5 | 0.8 | 49.91 |
| 0 | 0.75 | −5 | 0.7 | 87.06 |
| 0 | 0.75 | −5 | 0.6 | 183.77 |
| 0 | 0.75 | −5 | 0.5 | 521.34 |
| 0 | 0.75 | −5 | 0.45 | 1044.77 |
| 0 | 0.75 | −5 | 0.4 | 2491.14 |

In accordance with this disclosure, combining two or more calibration curves, each corresponding to a different time window post initiation of the reaction allows measurements to be made from the same reaction mix to cover a far broader range of analyte measurements than what was possible otherwise. For the simulated curves in the above example, the desire to cover the measuring range from 2-2500 au cannot be accomplished by a single dose-response curve. However, by collecting readings at 20 sec and 3000 sec from the same reaction mix after the reaction has been initiated and combining the two dose-response curves to evaluate any unknown within the measuring range between 2-2500 au extends the range.

Figure 8:
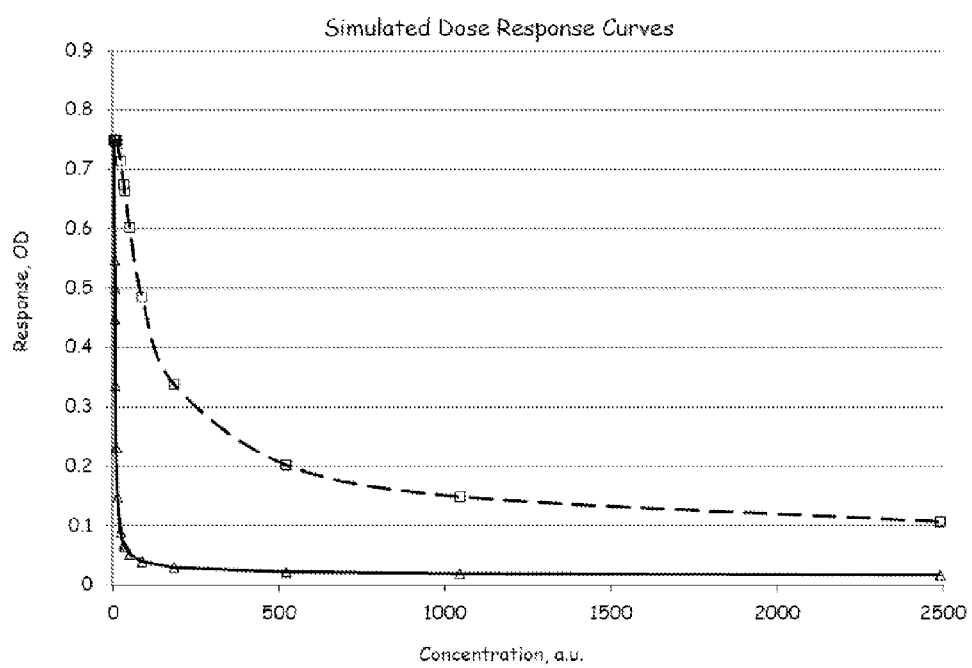
FIG. 8 shows the two dose-response curves that can be used together to span a greater analyte concentration range, each corresponding to different time windows post initiation of the reaction (at 20 sec (solid line) and 3000 sec (dashed line)).

FIG. 8 shows the two dose-response curves corresponding to time windows post initiation of the reaction at 20 sec (solid line) and 3000 sec (dashed line). These curves are used together to span the entire desired measuring range between 2-2500 au.

Specifically, the 20 sec calibration curve spans the range from 2-40 au, and the 3000 sec calibration curve spans the range from 30-2500 au. The two curves overlap between 30-40 au. The combination of these two calibration curves spans the entire range with an overlap region between 30-40 au. The overlap of the calibration curves facilitates a cross-over from one calibration curve to the other since when creating the calibration curves, test samples in this range can be read post initiation of the reaction at 20 seconds and 3000 seconds to ensure consistency and continuity.

The cross-over region provides a link for switching between the appropriate calibration curves. A desirable cross-over region ensures that the calibration curves consistently cover the entire measuring range.

In addition, the process of selecting the appropriate calibration curve can be automated. This makes the use of multiple calibration curves and measurement time windows no different than a single measurement time and a single calibration curve to an operator of a clinical diagnostic analyzer. A suitable clinical analyzer may be programmed to perform like a machine that is using a single calibration curve even though in practice multiple calibration curves corresponding to different observation time points are being used. Such a machine includes computer executable instructions that allow suitable incubation times, queuing, resource allocation in general to make possible the use of multiple calibration curves in evaluating an unknown sample of interest.

In another aspect, the time windows for observation may be selected to ensure a desired degree of accuracy. Thus, by combining several calibration curves, a desired degree of accuracy may be obtained in many instances where the signal does not vary as a linear function of the starting analyte concentration.

There are multiple ways to generate two overlapping calibration curves. Table 2 shows one such possible method using the Logit/Log 4 function, which requires a minimum of four calibrators to define the calibration function. In a preferred embodiment, there is at least one calibrator (also called a "standard") common to both calibration curves to assist with a smooth transition from one calibration curve to another.

TABLE 2

| Calibrator Level | 20 sec. Calibrators | 3000 sec. Calibrators |
|---|---|---|
| 1 | 2 au | |
| 2 | 5 au | |
| 3 | 12 au | 12 au |
| 4 | 35 au | 35 au |
| 5 | | 250 au |
| 6 | | 1000 au |
| 7 | | 2500 au |

Figure 9:
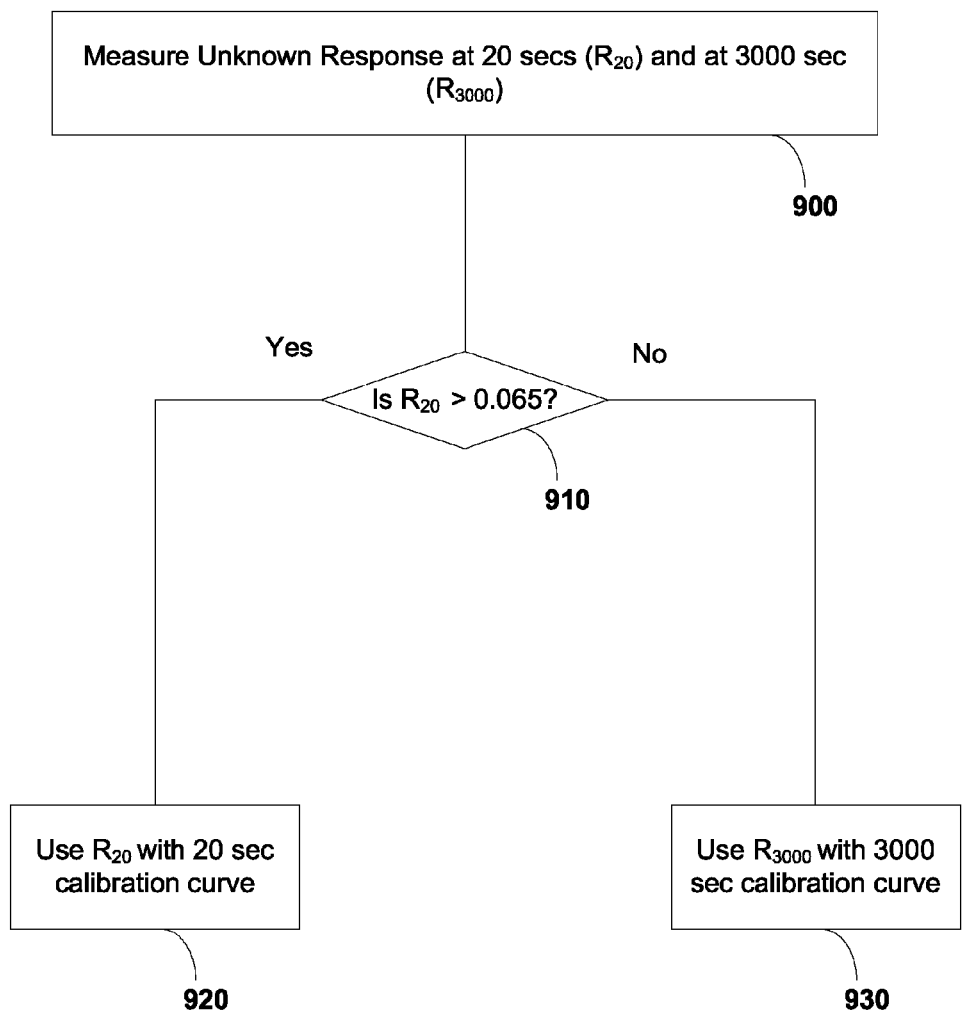
FIG. 9 depicts an illustrative flowchart showing how a particular dose-response curve is selected based on the signal strength. As shown, if the signal corresponding to the unknown analyte at the 20 sec window is greater than 0.065 then the 20 seconds dose-response curve is used. Else, the 3000 seconds dose-response curve is used.

Some exemplary methods for selecting which calibration curve to use for the determination of an unknown analyte concentration are illustrated next. The following exemplary example illustrates possible rules for using the two calibration curves shown in FIG. 8. As is shown in the flowchart of FIG. 9, when the response corresponding to the unknown analyte at the 20 sec window is greater than 0.065 (corresponding to a concentration of approximately 35 au), the signal from the 20 sec window will be analyzed on the 20 sec dose-response curve. If the response corresponding to the unknown analyte at the 20 sec window is less than 0.065, then instead of the signal from the 20 sec window, the signal from the 3000 sec window is analyzed using the 3000 sec dose-response curve (FIG. 9).

EXAMPLE

An inversely proportional clinical chemistry assay has a standard protocol to measure the response 161.5 seconds after the addition of the last reagent. In this example, the protocol was altered to measure responses at 9.5 seconds, 161.5 seconds, and 275.5 seconds in a single reaction cuvette after the addition of the last reagent to enable the evaluation of both the dual dose-response curve model and the standard assay protocol model. In the description that follows, the response measured at 9.5 seconds after reagent addition is called the "Early" dose, the response measured at 161.5 seconds after reagent addition is called the "Standard" dose, and the response measured at 275.5 seconds after reagent addition is called the "Late" dose. The early dose and the late dose calibration curves are combined in to form the "Dual" dose-response.

Seven calibrators were run in the experiment and used to calibrate the three separate dose-response curves as specified in Table 3. As described above in the necessary requirements for the multiple dose-response model, the early and late dose-response curves share at least one calibrator in the cross-over region to cover the entire measuring range in a continuous manner. In this particular example, the early and late dose-response curves share two calibrators in common (0.449 g/dL and 0.84 g/dL) to assist in the cross-over region between the early and late dose-response curves.

TABLE 3

| Calibrator Level | Calibrator Concentration (g/dL) | Std. Assay | Early Dose | Late Dose |
|---|---|---|---|---|
| 1 | 0 |  | X |  |
| 2 | 0.217 |  | X |  |
| 3 | 0.449 | X | X | X |
| 4 | 0.84 | X | X | X |
| 5 | 1.447 | X |  | X |
| 6 | 2.083 | X |  | X |
| 7 | 2.604 | X |  | X |

Figure 10:
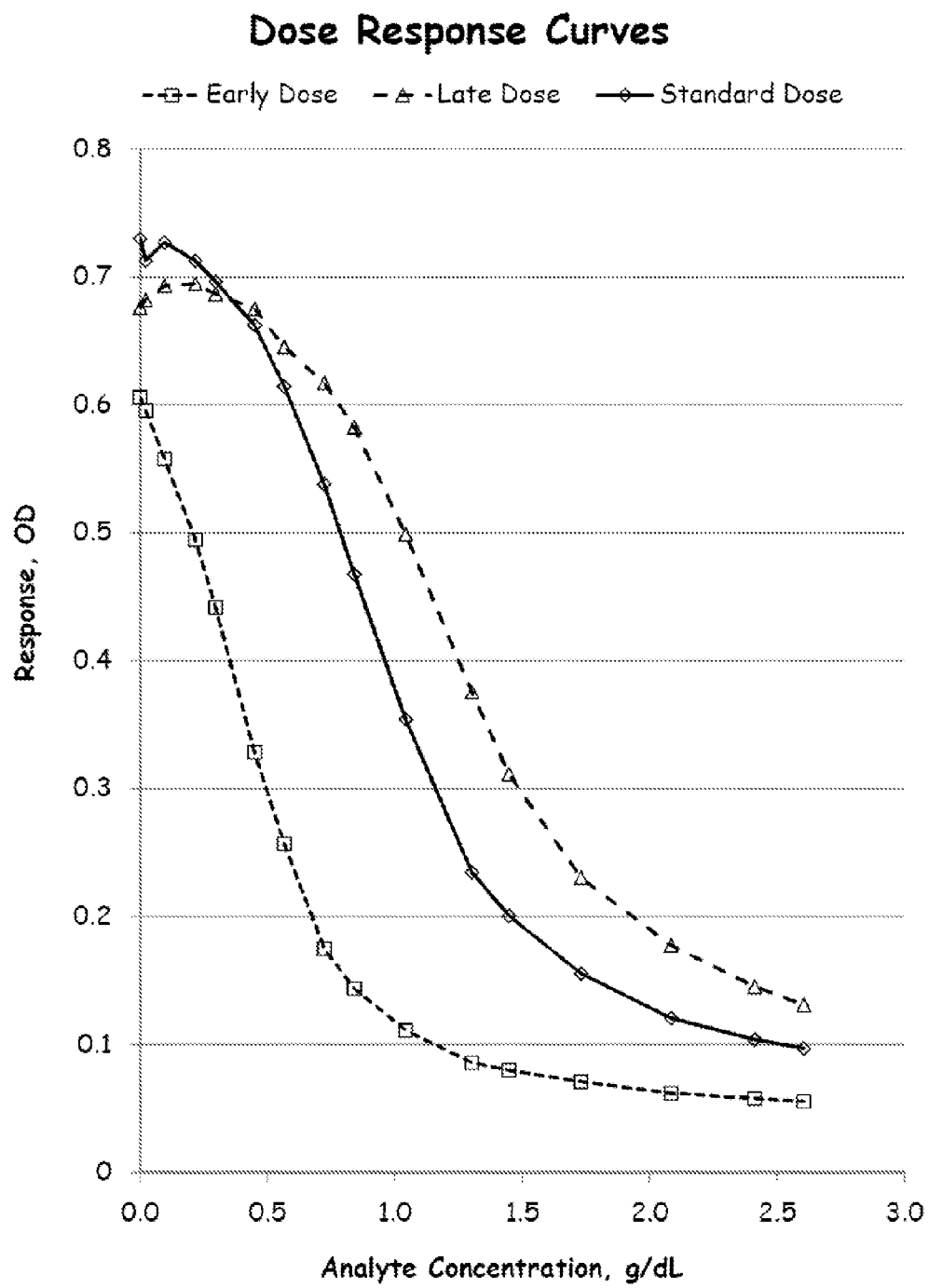
FIG. 10 shows three calibration curves corresponding to measurements taken at 9.5 seconds after reagent addition (the "Early" dose), at 161.5 seconds after reagent addition (the "Standard" dose), and at 275.5 seconds (the "Late" dose) to illustrate the effect of the selection of the time window on the measurement accuracy. The illustrative curves share two calibrators in common (0.449 g/dL and 0.84 g/dL) to assist in the cross-over region between the early and late dose-response curves.

In addition to the calibrators, multiple fluids that span the measuring range from 0.2-2.6 g/dL were run in triplicate to demonstrate the true shape of the dose-response curve for each of the three different protocols, which are shown in FIG. 10. The standard dose-response curve (diamonds) shows a flattening of the dose-response curve at 0.217 g/dL on the low end and at 2.411 g/dL on the high end. This flattening shape limits the effective measuring range of the assay based on the response function alone to approximately 0.2-2.4 g/dL. The early dose-response curve (squares) shows no flattening on the low end and flattening on the high end at 1.302 g/dL, providing an effective measuring range of the assay based on the response function alone to approximately 0-1.3 g/dL. The late dose-response curve (triangles) shows a flattening of the dose-response curve at 0.449 g/dL on the low end and no flattening on the high end, providing an effective measuring range of the assay based on the response function alone to approximately 0.5-2.6 g/dL.

Each of the three dose-response curves was calibrated using the Logit/Log 4 calibration model (Equation 1) with calibrator levels indicated in Table 3. The Logit/Log 4 calibration curves for the three response times are shown with fine broken lines corresponding to the Early calibration curve, the solid line to Standard calibration curve and the rough broken line corresponding to the Late calibration curve in FIG. 11. Both the Standard and Late calibration curves show the expected flattening of the calibration curves at early times, limiting the effective measuring range more than by the dose-response curve shape alone as described above. The Early calibration curve shows a deviation from the data at higher concentrations since not all calibrator levels were used in the calibration.

Figure 11:
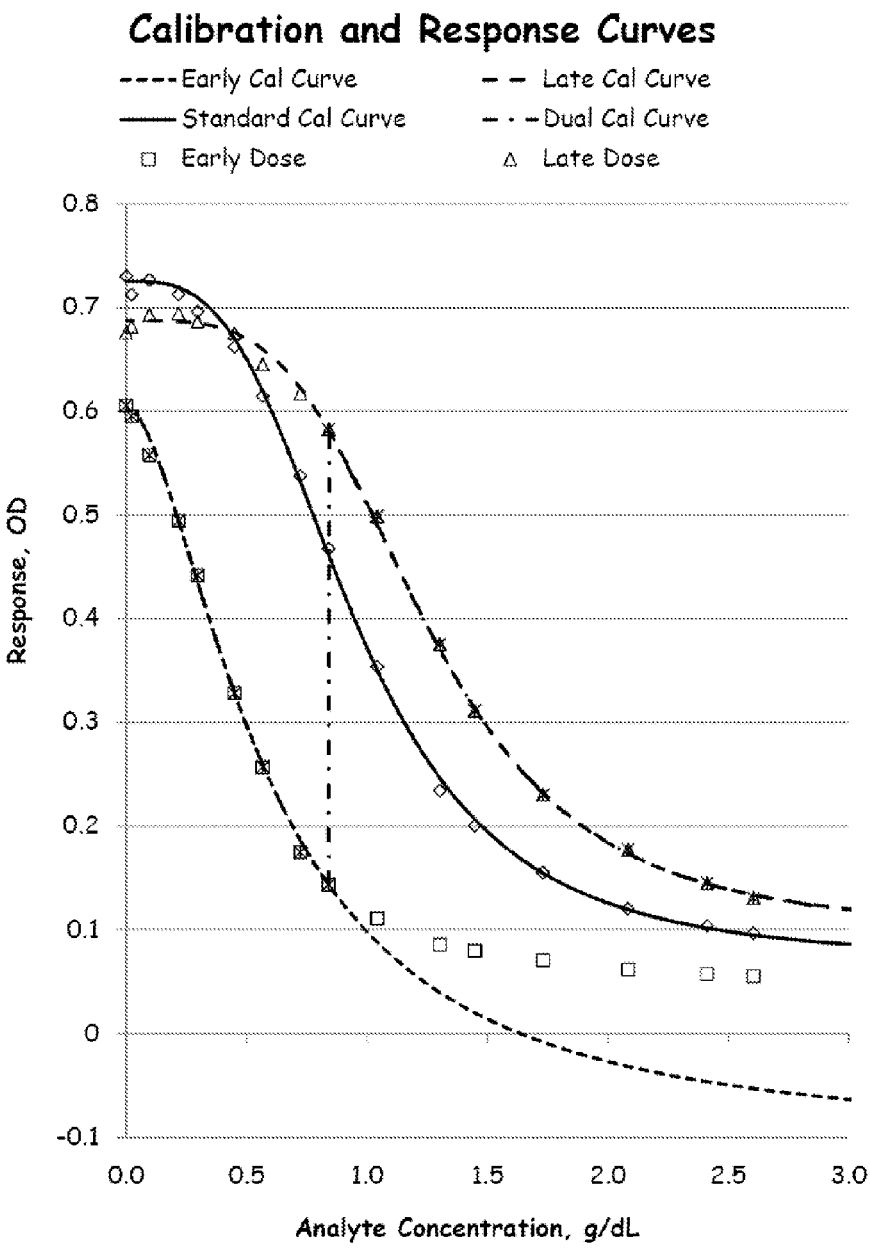
FIG. 11 shows calibration curves corresponding to measurements taken at 9.5 seconds after reagent addition (the "Early" dose) and at 275.5 seconds (the "Late" dose) combined to get a dual calibration curve implementation.
Figure 12:
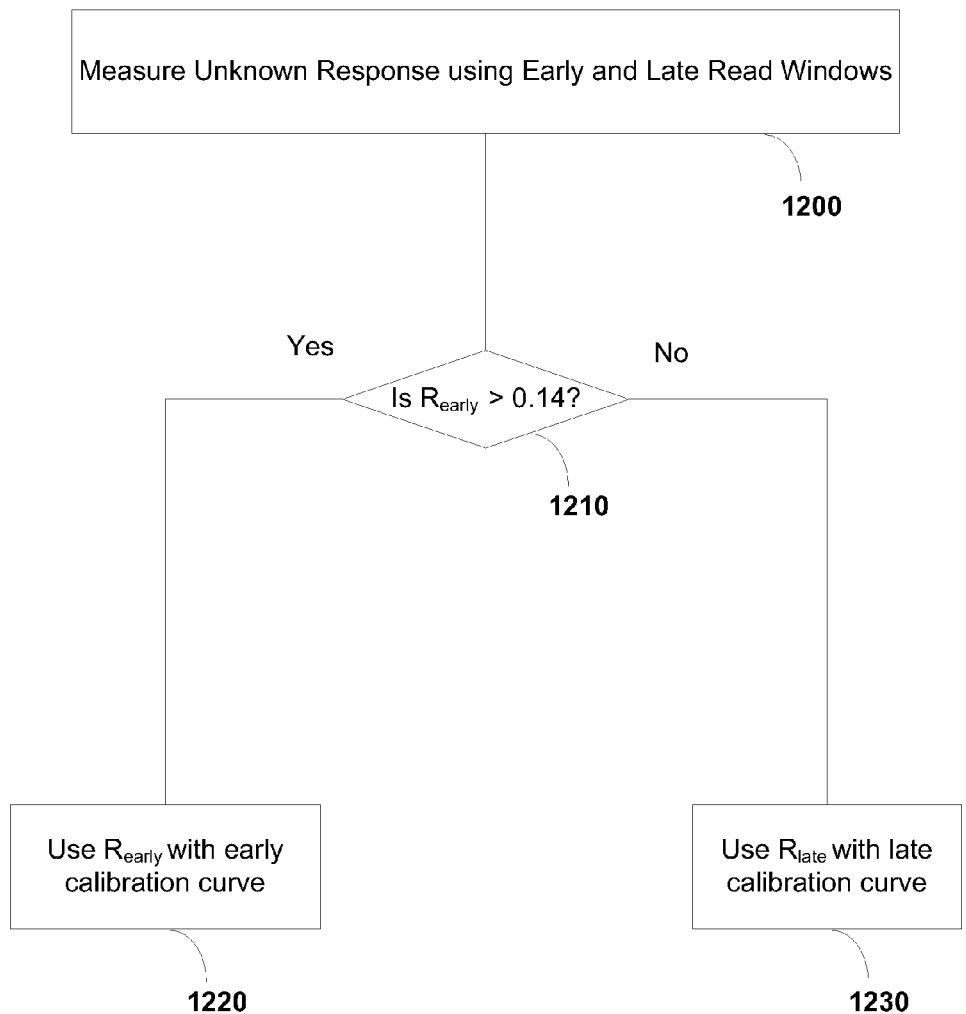
FIG. 12 illustrates these cross-over rules in operation by way of a diagram showing the decision making logic to guide the choice of the calibration curve to use in the manner similar to that in FIG. 9.

FIG. 11 shows a dual dose calibration curve for the data of FIG. 10. The dual dose calibration curve of the disclosure is shown in black and transitions from the early calibration curve to the late calibration curve at the cross-over response of 0.14 OD on the early calibration curve (corresponding to a concentration of ~0.84 g/dL). FIG. 12 illustrates these cross-over rules in operation by way of a diagram showing the decision making logic to guide the choice of the calibration curve to use in the manner similar to that in FIG. 9.

A benefit of the current disclosure is the extended measuring range and the enhanced precision and accuracy. The extended measuring range has been qualitatively described above based on the curvature of the calibration curves seen in FIG. 8 and FIG. 11. A dual dose calibration curve has no or little flattening at either the low or high concentrations. The extended measuring range can be easily seen in the accuracy of the test fluids' predicted concentration from the dual dose calibration curve verses the early, standard, or late calibration curve analysis (FIG. 13).

Figure 13:
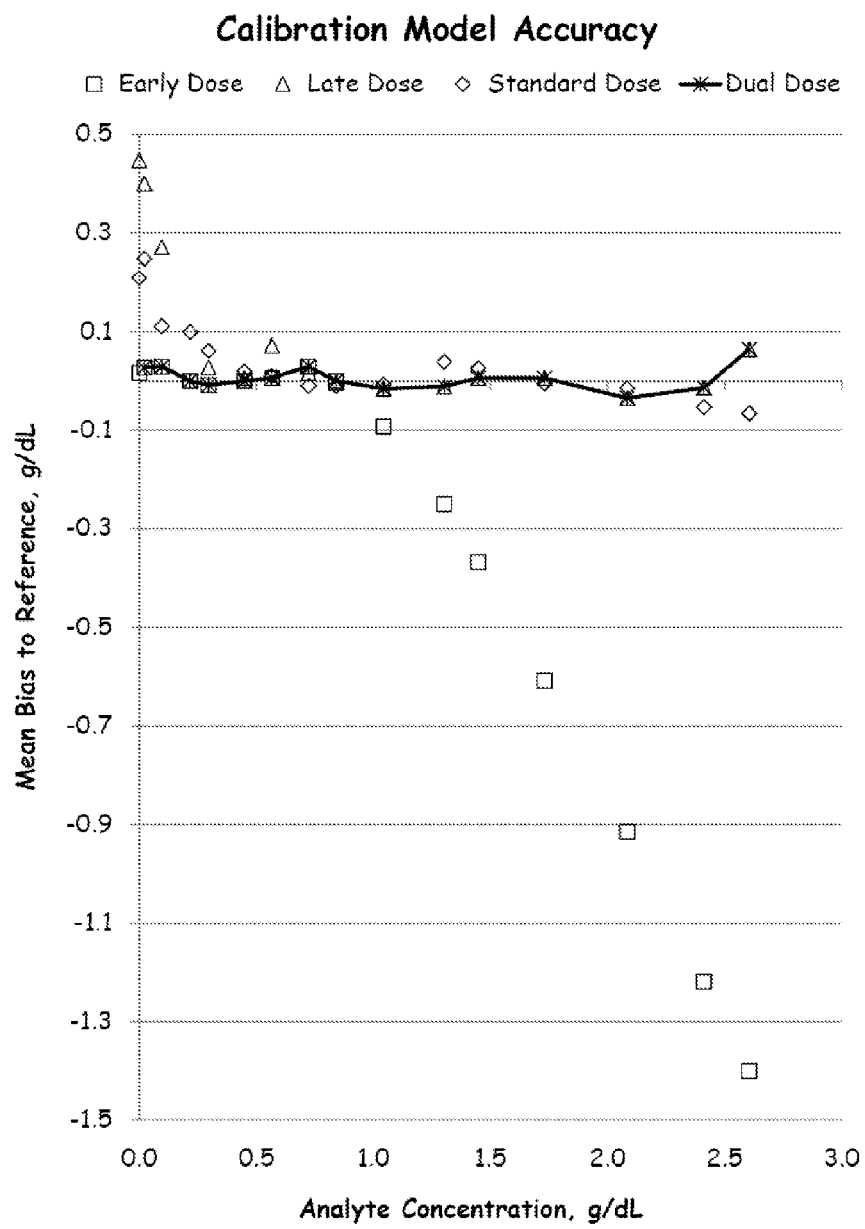
FIG. 13 shows the mean bias between the predicted analyte level for each sample and the reference analyte level. The early dose-response curve deviates significantly from the calibration curve, so the bias is large for all sample concentrations greater than 0.84 g/dL. Both the standard and late dose-response curves significantly deviate from zero bias at lower concentration due to the flattening of the dose-response curve.

FIG. 13 shows the mean bias between the predicted analyte level for each sample (Table 4) versus the reference analyte level assigned to each sample. The early dose-response curve deviates significantly from the calibration curve, so the bias is large for all sample concentrations greater than 0.84 g/dL. Both the standard and late dose-response curves significantly deviate from zero bias at lower concentration due to the flattening of the dose-response curve and lack of a model fit. Only the dual dose model, the subject of this disclosure, shows excellent agreement with the reference concentration throughout the entire measuring range (≤0.1 g/dL bias) by transitioning between the Early and Late Dose-Response curves to better utilize each calibration curve and demonstrates the benefit of the extended measuring range with the assay performance.

TABLE 4

| Sample ID | Reference Conc. (g/dL) | Early Dose Conc. (g/dL) | Late Dose Conc. (g/dL) | Std. Assay Conc. (g/dL) | Dual Dose Conc. (g/dL) |
|---|---|---|---|---|---|
| 1 | 0 | 0.016 | 0.447 | 0.209 | 0.016 |
| 2 | 0.022 | 0.049 | 0.423 | 0.270 | 0.049 |
| 3 | 0.096 | 0.125 | 0.367 | 0.207 | 0.125 |
| 4 | 0.217 | 0.217 | ME* | 0.316 | 0.217 |
| 5 | 0.296 | 0.288 | 0.323 | 0.357 | 0.288 |
| 6 | 0.449 | 0.449 | 0.455 | 0.469 | 0.449 |
| 7 | 0.566 | 0.572 | 0.638 | 0.576 | 0.572 |
| 8 | 0.723 | 0.752 | 0.739 | 0.713 | 0.752 |
| 9 | 0.840 | 0.840 | 0.836 | 0.830 | 0.840 |
| 10 | 1.042 | 0.950 | 1.026 | 1.035 | 1.026 |
| 11 | 1.302 | 1.052 | 1.291 | 1.341 | 1.291 |
| 12 | 1.447 | 1.080 | 1.453 | 1.473 | 1.453 |
| 13 | 1.730 | 1.122 | 1.736 | 1.725 | 1.736 |
| 14 | 2.083 | 1.169 | 2.048 | 2.069 | 2.048 |
| 15 | 2.411 | 1.192 | 2.397 | 2.358 | 2.397 |
| 16 | 2.604 | 1.204 | 2.668 | 2.538 | 2.668 |

*ME—Mechanical Error—no result reported

Figure 14:
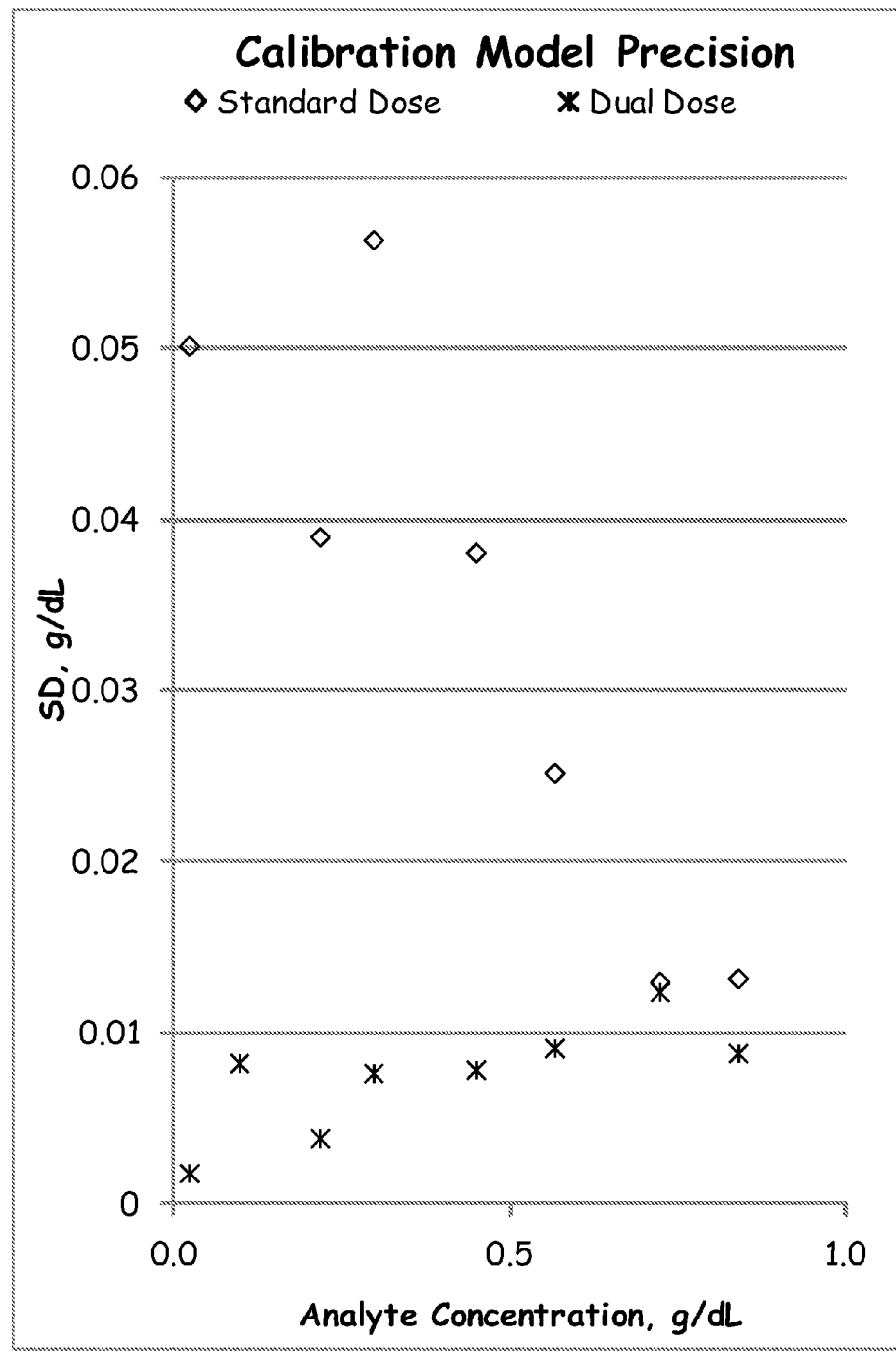
FIG. 14 shows the standard deviation for the dual dose-response model is favorably below that for the standard dose-response curve even though the dual dose-response curve covers a larger range.

Besides the improvement in accuracy throughout the measuring range enabled by the dual dose-response model, see, e.g., FIG. 13, the low end imprecision is also substantially reduced in the dual dose-response model of this disclosure. As is shown in FIG. 14, the SD for the dual dose-response model is ≤0.01 g/dL for measuring analyte levels below 0.5 g/dL, which is significantly better than the imprecision for standard dose-response curve (>0.035 g/dL) over the same range. This improvement in precision is accompanied with a 3-fold increase in response range for the dual dose model verses the standard model (0.34 OD vs. 0.11 OD) in the range between 0 and 0.5 g/dL.

The dual dose-response model offers a larger signal range throughout the measuring range compared to the signal for the standard model. Table 5 shows the nearly 50% increase in OD range for the dual dose-response model over the standard dose-response model. This causes a dramatic improvement in the precision at low levels of analyte as described above.

The expanded OD range further accompanies improvements in the accuracy of the dose-response curve slope at both lower and higher analyte concentrations, as is shown in FIG. 13 in the dual dose-response model spanning a measuring range beyond the current 2.6 g/dL. The high concentration end slope (between 2.4-2.6 g/dL) is more than twice as large for the dual dose-response model (Table 6) than for the Standard dose-response curve.

TABLE 5

| Concentration Range | Standard Dose | Standard Dose OD Range | Dual Dose | Dual Dose OD Range |
|---|---|---|---|---|
| 0-0.84 g/dL | 0.73-0.47 | 0.26 | 0.61-0.14 | 0.47 |
| 0.84-2.6 g/dL | 0.47-0.1 | 0.37 | 0.58-0.13 | 0.45 |
| 0-2.6 g/dL | | 0.63 | | 0.92 |

TABLE 6

| | Single Dose | Dual Dose |
|---|---|---|
| Slope (2.4-2.6 g/dL) | −0.036 | −0.074 |

Although there is great flexibility in using the more than two dose-response curves as described herein, the measuring range of most processes of interest are fairly narrow that they can be covered with two different dose-response curves. The preferred mode therefore uses two calibration curves. In addition, in the preferred embodiment calibrators are shared in generating the dose-response curves by the simple modicum of reading the same calibrator at two different times, which limits the total number of calibrators required to generate the dose-response curves. This further reduces the time and cost of the calibration itself.

Preferably, the cross-over point is at or very near one of the common calibrator concentrations to ensure a continuous predicted concentration between the two different dose-response curves. The continuity is also enhanced when there is a substantial cross-over region where both calibration curves provide essentially the same measured levels of the analyte regardless of the time window used.

Many alternative mathematical models (other than Logit/Log 4) could be used to describe the calibration curves. The preferred models need not be changed from those that are known to work well for the single dose-response model already in use in the field. Some examples of mathematical models for describing the multiple dose-response curves are linear, polynomial, cubic spline, Logit/Log 4, and Logit/Log 5.

A Scheduler is the brains making the analyzer subsystems work together. The Scheduler performs scheduling functions, for instance, to allocate resources to samples input in any order, without regard to the type or quantity of tests required, and to maintain or improve the throughput of the analyzer. The Scheduler ensures that samples are accepted from an input queue as resources are reserved for the various expected tests or steps relevant to a particular sample. Unless the required resources are available, a sample continues to be in the input queue. In a preferred analyzer model, the sample is aspirated and then sub-samples are taken from this aspirated volume for various tests. The operation of the Scheduler together with the types of tests supported by the analyzer provides a reasonably accurate description of an analyzer under consideration.

A preferred Scheduler includes the synergistic effects of two-dimensional random access to the input samples while providing access to resources including, for example, multiple platforms, supply of consumables including thin film slides, reaction vessels and cuvettes, along with a plurality of sensiometric devices such as electrometers, reflectometers, luminescence, light transmissivity, photon detection, an incubator for heating the samples, a supply of reagents, and a plurality of reagent delivery subsystems, all of which can be accessed and used readily.

Implementing FIGS. 9 and 12 preferably is with the aid of a Scheduler that allocates tentative times for completion of a test. This is useful since a second time window may need to be allocated together with a specification of the corresponding calibration curve. Such a Scheduler handles samples to optimize throughput and processing of samples to ensure the extended analyte range is utilized by allocating additional resources to a sample as needed. Such a Scheduler preferably converts the clinical laboratory analyzer of FIG. 1 into one that supports measuring far broader ranges of analyte concentrations by programming it to implement the new Scheduler functionality. This programming may be by way of programming languages or graphical programming interfaces and delivered in the form of an update.

Figure 1:
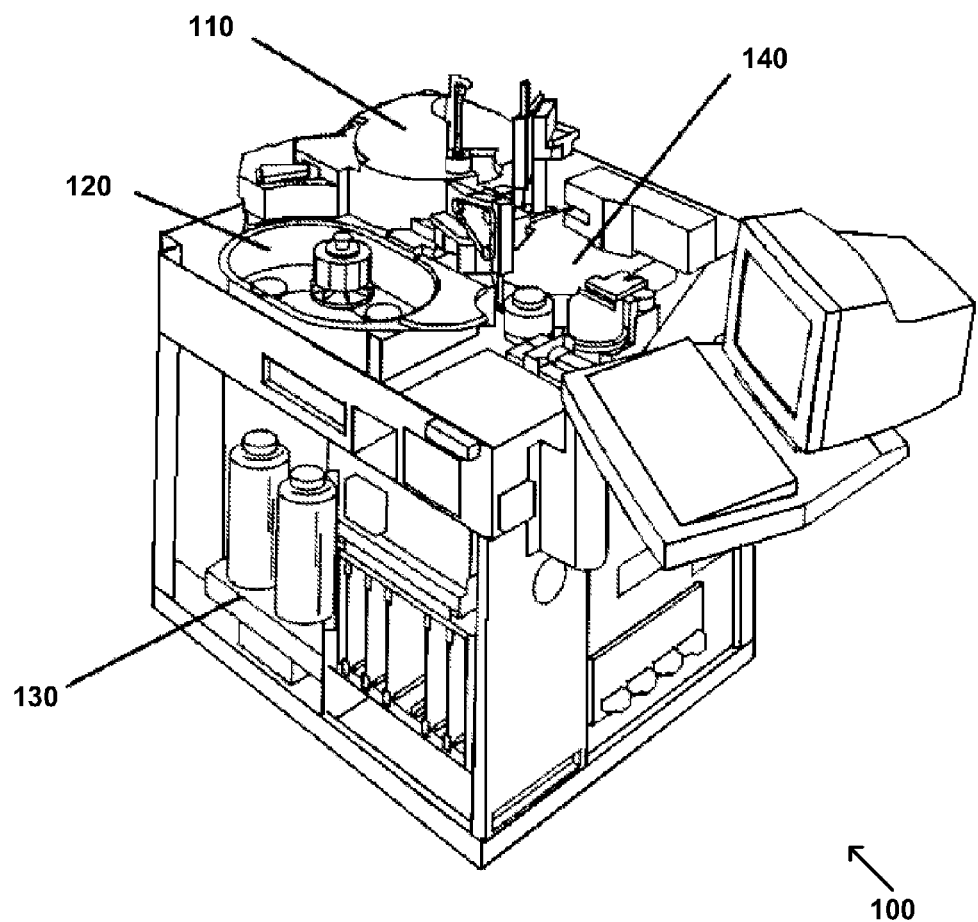
FIG. 1 (Prior Art) depicts a prior art clinical diagnostic analyzer and its major subsystems.
Figure 2:
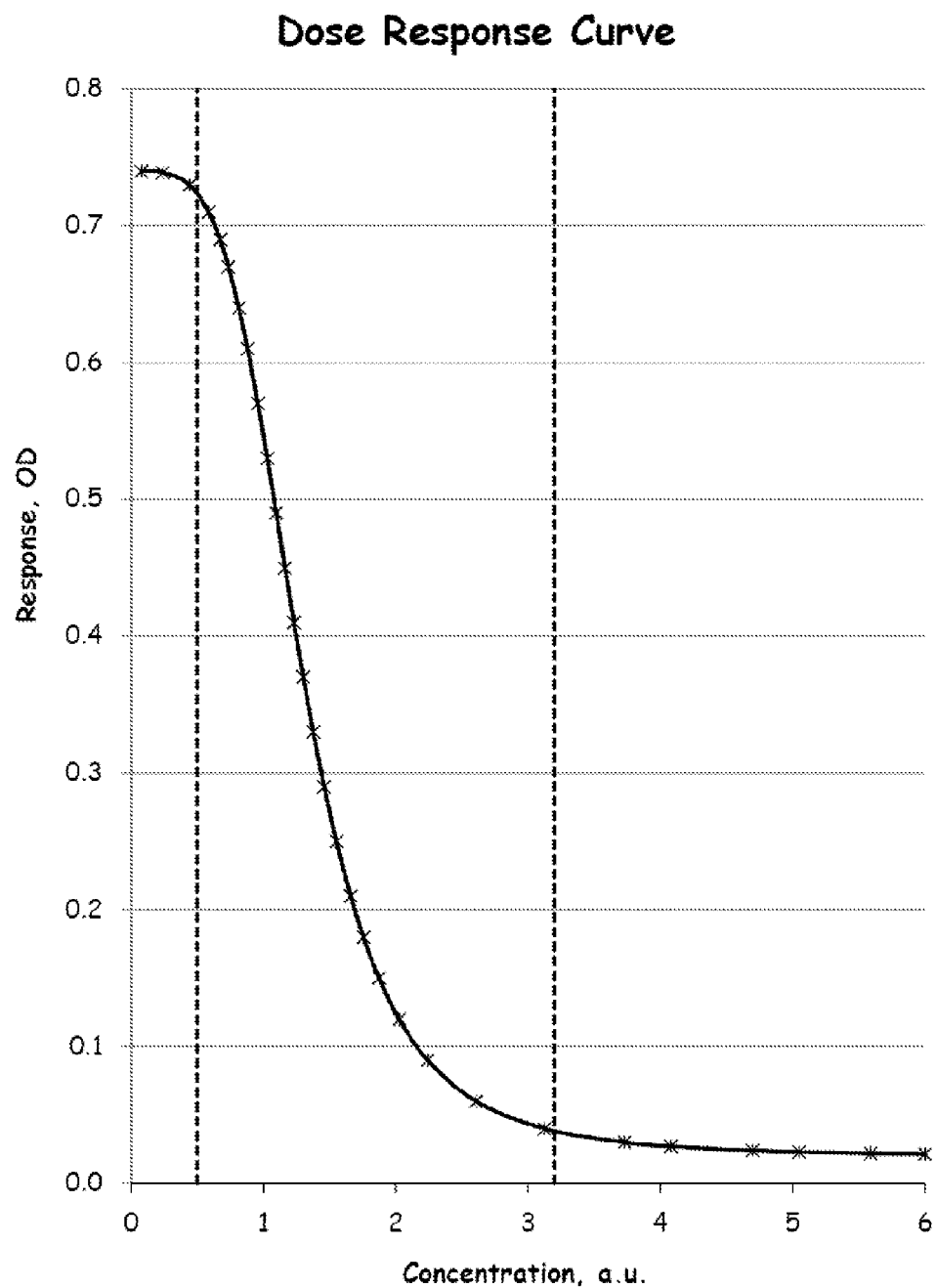
FIG. 2 (Prior Art) shows an exemplary dose-response curve.
Figure 3:
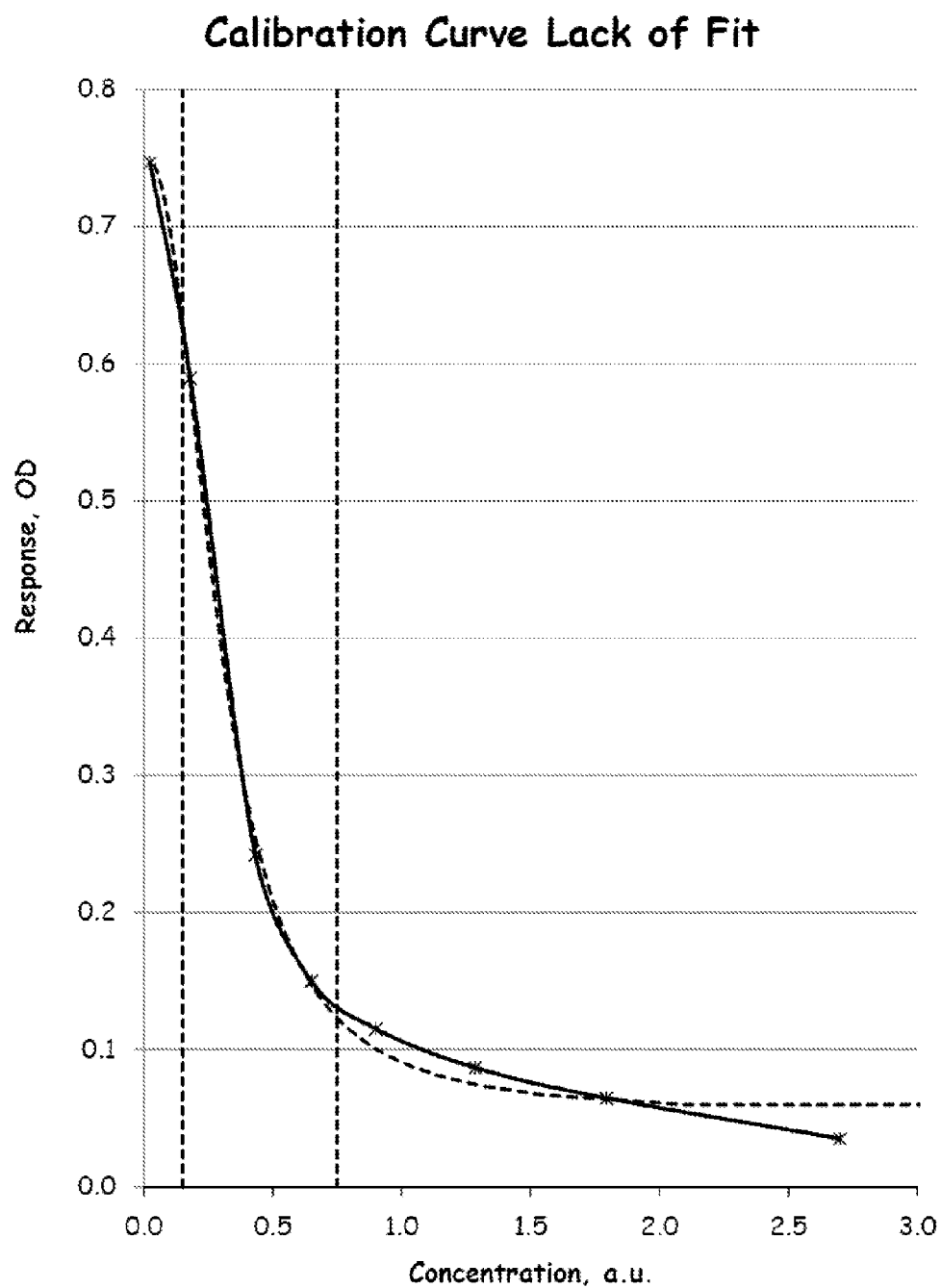
FIG. 3 (Prior Art) shows the challenges in fitting a calibration curve to data covering a broad measurement range.

For implementing the multiple calibration curves in a clinical diagnostic analyzer, such as the one illustrated in FIG. 1, a preferred method modifies the Scheduler to permit signal measurement at different times based on a prior signal strength measurement. In effect, this is an implementation of the decision logic similar to that illustrated in FIGS. 9 and 12 in a clinical diagnostic analyzer.

Turning to FIG. 9, it shows a method for implementing an extended range. During step 900, a module determines a signal level in a sample of interest during a first time window—here the exemplary time window is at about 20 seconds. Then control passes to step 910 during which the signal strength is compared to a threshold—such as the illustrative threshold of 0.065—to transfer control to step 920 if the threshold is exceeded, or, alternatively to step 930 if the threshold is not exceeded. If control is passed to step 920, the 20 second calibration curve is used while if control is passed to step 930, the 3000 seconds calibration curve is used to convert the signal strength into an analyte level.

Similarly, in FIG. 12, during step 1200, a module determines a signal level in a sample of interest using both the Early and Late read windows. Then control passes to step 1210 during which the analyte response based on the Early read window is compared to a threshold—such as the illustrative threshold of 0.14—to transfer control to step 1220 if the threshold is exceeded, or, alternatively to step 1230 if the threshold is not exceeded. If control is passed to step 1220, the Early calibration curve is used while if control is passed to step 1230, the Late calibration curve is used to convert the signal strength into an analyte level.

Figure 15:
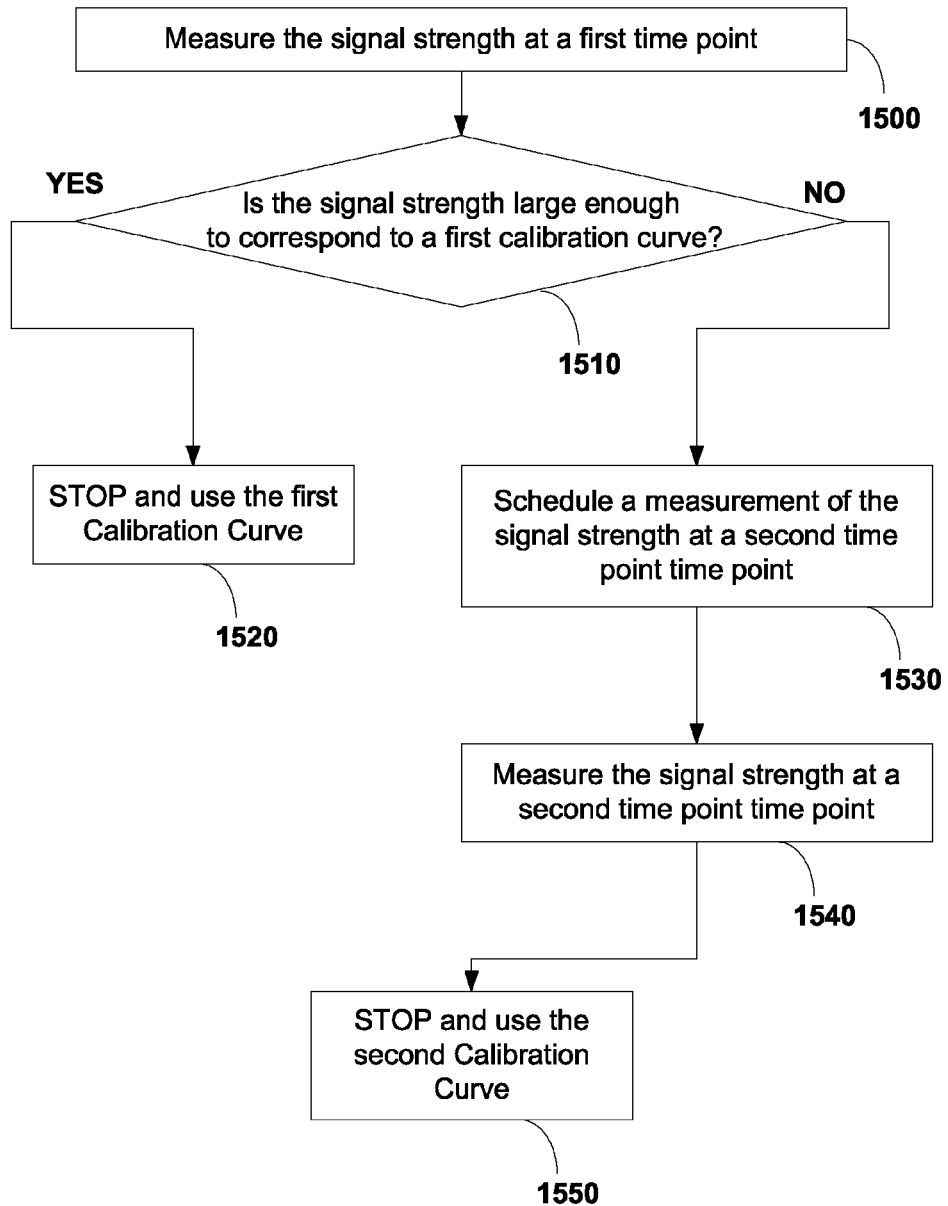
FIG. 15 shows a flow diagram illustrating implementations of a method using the dual calibration curve for extending the range and improving the accuracy in measuring an analyte of interest.
Figure 16:
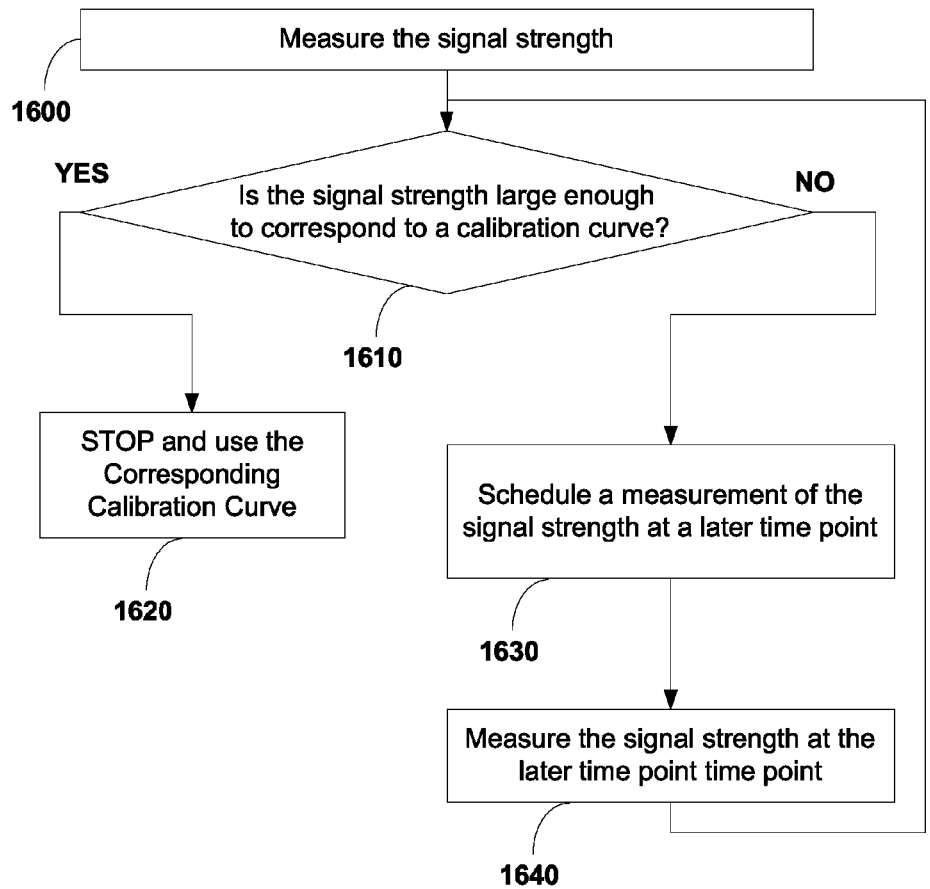
FIG. 16 shows a flow diagram illustrating implementations of a method using the multiple calibration curves for extending the range and improving the accuracy in measuring an analyte of interest.

FIGS. 15 and 16 show flow diagrams illustrating implementations of the dual and multiple calibration curve based methods for extending the range and improving the accuracy in measuring an analyte of interest. In FIG. 15, during step 1500 the signal strength is measured at a first time point. Herein the term 'signal strength' encompasses various possible units in which a signal may be measured or converted. Control then passes to step 1510, during which if the signal strength is large enough, control passes to step 1520, during which the first calibration curve is used. Alternatively during step 1510 if the signal strength is not large enough, control passes to step 1530. During step 1530 a measurement at a second time point is scheduled and control passed to step 1540. During step 1540 the signal strength is measured at the second time point and control passes to step 1550 for use of the second calibration curve for measuring the level of the analyte of interest.

FIG. 16 illustrates a more general scheme. In FIG. 16, during step 1600 the signal strength is measured. Control then passes to step 1610, during which if the signal strength is large enough, control passes to step 1620, during which the corresponding calibration curve is used. In effect, the method determines if there is a suitable corresponding first (or second or third and the like) calibration curve. In the absence of a suitable calibration curve, a later time point for determining the signal strength from the reaction mix is scheduled. Accordingly, during step 1610 if the signal strength is not large enough, control passes to step 1630. During step 1630 a measurement at a later (which could be a second or third and the like) time point is scheduled and control passed to step 1640. During step 1640 the signal strength is measured at the later time point and control passes back to step 1610 and then onto identification of a suitable calibration curve. If there are multiple calibration curves corresponding to different signal magnitudes or time points, that may be used, then the level of the analyte may be determined from just one or more than one calibration curve.

Figure 17:
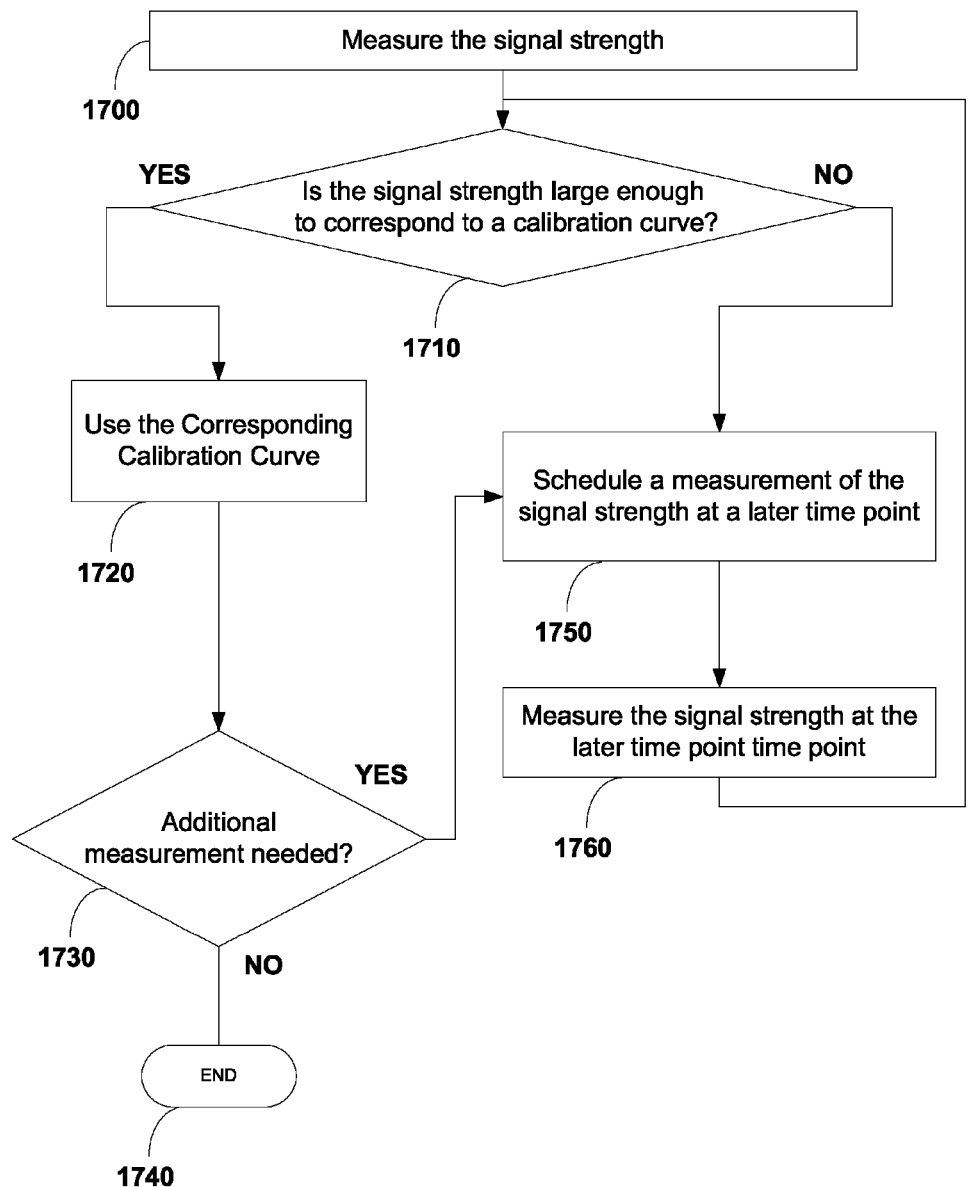
FIG. 17 shows a flow diagram illustrating implementations of a method using more than one calibration curve to allow measurement of the same reaction at different times—and possibly averaging the results to improve accuracy or track errors.

In FIG. 17 is illustrated a method for using more than one calibration curve to allow measurement of the same reaction at different times—and possibly averaging the results to improve accuracy or track errors. For such averaging advantageously a weighted mean of analyte levels measured at different times may be used to further refine the results. In FIG. 17, during step 1700 the signal strength is measured. Control then passes to step 1710, during which if the signal strength is large enough, control passes to step 1720, during which the corresponding calibration curve is used. Control passes from step 1720 to step 1730 to determine if additional measurements are desired at later time points. The method terminates if no additional measurements are desired with control passing to step 1740. However, if additional measurements are desired at later time points, then control passes to step 1750, during which a later measurement is scheduled. Control passes to step 1760 for making the scheduled measurement, following which control loops back to step 1710. In effect, the method also determines if there is a suitable corresponding first (or second or third and the like) calibration curve. In the absence of a suitable calibration curve, a later time point for determining the signal strength from the reaction mix is scheduled—as well as for just determining a second or more measurements from the same reaction mix. Multiple measurements may be averaged.

Figure 18:
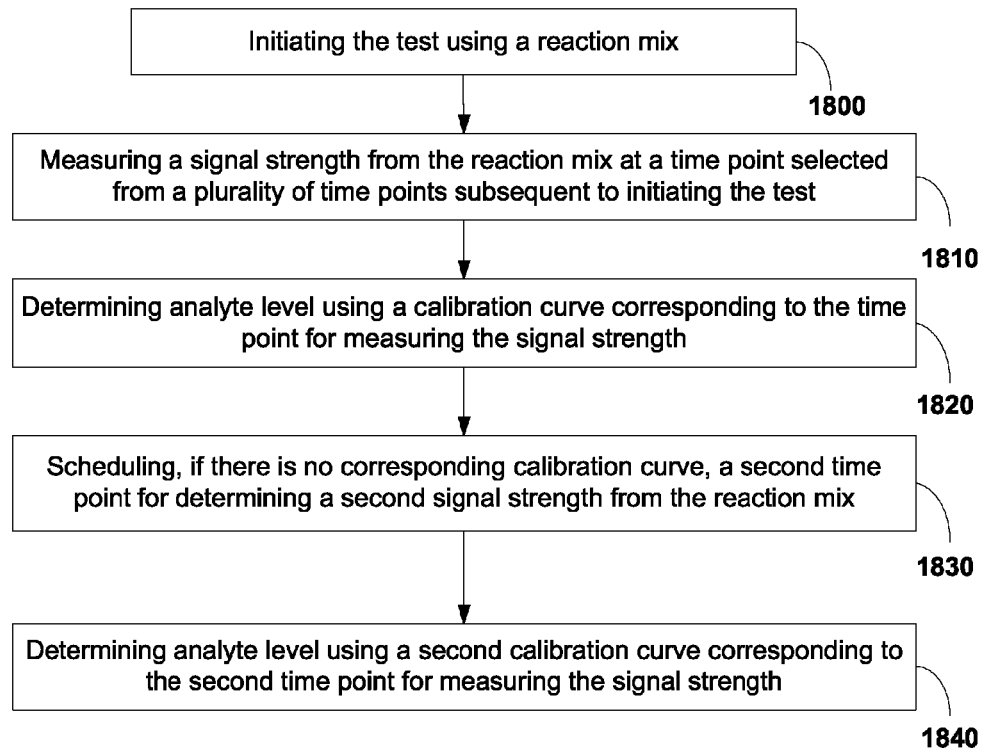
FIG. 18 shows a flow diagram illustrating implementations of a method using the dual calibration curve for extending the range and improving the accuracy in measuring an analyte of interest.

In FIG. 18 is illustrated a method for using more than one calibration curve to allow measurement in a clinical diagnostic analyzer. In FIG. 18, during step 1800 the reaction is initiated. Control then passes to step 1810, during which a signal strength from the reaction mix at a time point selected from a plurality of time points subsequent to initiating the test is measured. Control then passes to step 1820, during which the analyte level is determined using a calibration curve corresponding to the time point for measuring the signal strength the signal strength is large enough. Then control passes to step 1830, during which a second time point for determining a second signal strength from the reaction mix is scheduled if there is no corresponding calibration curve. Control passes from step 1830 to step 1840 to determining the analyte level using a second calibration curve corresponding to the second time point for measuring the signal strength.

Figure 19:
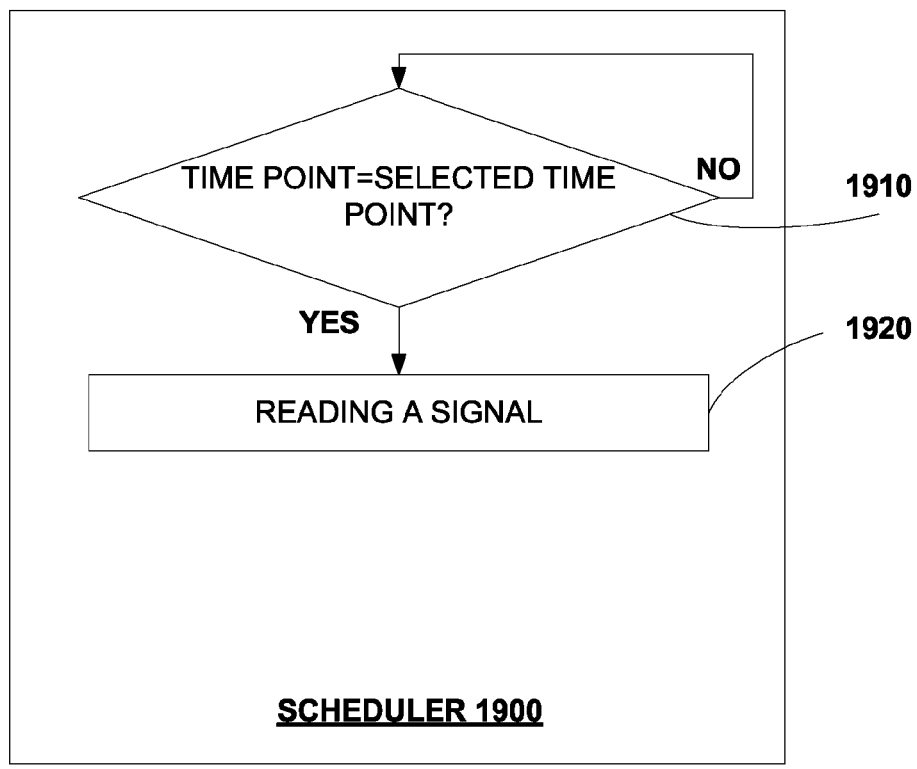
FIG. 19 shows a scheduler implement reading a signal at a time point.

FIG. 19 depicts a scheduler 1900 for use in a diagnostic clinical analyzer supporting an extended range. The scheduler implements reading a signal at a time point by checking if the time point has been reached during step 1910 and then scheduling the signal during step 1920. If during step 1910 the time point is not reached, the control loops back. This looping back is show as being a direct loop for clarity. In practice, a preferred embodiment will have the scheduler attend to other tasks before testing the time point again. In a preferred embodiment, the selected time point corresponds to a calibration curve selected from a plurality of calibration curves based on the signal. The signal so read during step 1920 is mapped into a measured value of an analyte of interest using the selected calibration curve.

Many of the limitations on the measuring range of diagnostic and other tests can be overcome by implementing the multiple dose-response model of this disclosure. The description herein shows the enhancements to extend the measuring range, and the example shows the theoretical model put into practice with a real improvement for increased measuring range for the assay described. In addition to the extended measuring range, the disclosure also demonstrates an improvement in the test method precision due to the increased response range and in the test method accuracy due to the improved fitting of the calibration curve. By the improvements offered from the multiple dose-response model, the shortcomings on the measuring range and precision from current model have been eliminated.

One skilled in the art will appreciate that the above disclosure is susceptible to many variations and alternative implementations without departing from its teachings or spirit. The scope of the claims appended below includes such modifications. Further, each reference discussed and cited herein is hereby incorporated herein by reference in its entirety.

I claim:

1. A method for extending the range of a single assay and for measuring an analyte level of the assay based on a time-variant signal reflecting a dynamic response level in an instrument, the method comprising:

using a first calibration curve representative of analyte level and response level of the assay at a first time point subsequent to initiation of the assay to generate the analyte level if a signal strength corresponds to a predefined signal level for the first time point; and if the signal strength fails to correspond to the predefined signal level for the first time point, then using a second calibration curve representative of analyte level and response level of the assay at a second time point subsequent to the first time point to estimate the analyte level if the signal strength corresponds to a predefined signal level for the second time point.

2. A method for measuring a level of an analyte using a plurality of calibration curves, each calibration curve associated with at least one threshold in regard to a single reaction at a corresponding plurality of fixed time points after initiation of the single reaction, the method comprising:

determining whether a first condition is met based on comparing a measured signal level with a first predetermined threshold associated with a first calibration curve from the plurality of calibration curves is satisfied at a first time point subsequent to initiation of the reaction, in which the first calibration curve is representative of signal levels and corresponding analyte levels at the first time point, and if the first condition is satisfied then using the first calibration curve to generate a first measured value for the level of the analyte; and determining whether a second condition is met based on comparing a measured signal level at a second time of the reaction with a second predetermined threshold associated with a second calibration curve from the plurality of calibration curves at the second time point.

3. The method of claim 2, wherein if more than one calibration curve from the plurality of calibration curves are available for measuring the level of the analyte, due to thresholds corresponding to each of the more than one calibration curve being satisfied at corresponding time points of the single reaction, then using an average of analyte levels corresponding to each of the available calibration curves as the measured level of the analyte.

4. The method of claim 3, wherein the average is a weighted average of the analyte levels of the available calibration curves.

5. The method of claim 2, wherein the first condition requires that a signal corresponding to the level of the analyte exceed the first threshold.

6. The method of claim 2, wherein the first condition requires that a signal corresponding to the level of the analyte be less than the first threshold.

7. The method of claim 2, wherein the first condition requires that a signal corresponding to the level of the analyte be equal to the first threshold.

8. The method of claim 2, wherein the second condition requires that a signal corresponding to the level of the analyte exceed the second threshold.

9. The method of claim 2, wherein the second condition requires that a signal corresponding to the level of the analyte be less than the second threshold.

10. The method of claim 2, wherein the second condition requires that a signal corresponding to the level of the analyte be equal to the second threshold.

11. A method for scheduling a test in a clinical analyzer supporting an extended range, the method comprising the steps of:

initiating the test using a reaction mix;

determining a first signal strength from the reaction mix at a first predefined time point after initiating the test;

determining whether there is a suitable first calibration curve corresponding to the first predefined time point by comparing the determined first signal strength with a first predetermined threshold signal level of the first calibration curve, wherein the first calibration curve is suitable if the determined first signal strength at least equals the first predetermined threshold signal level;

scheduling, if there is no suitable first calibration curve, a second predefined time point after initiating the test for determining a second signal strength from the reaction mix;

determining, at the second predefined time point, the second signal strength;

identifying a second calibration curve corresponding to the second predefined time point and determining if the second calibration curve is suitable by comparing the determined second signal strength with a second predetermined threshold signal level of the second calibration curve; and determining a level of an analyte from one or more of the first signal strength and second signal strength.

12. A diagnostic clinical analyzer supporting an extended range comprising a scheduler for implementing the reading of a signal at a time point following initiation of a single assay, the time point of the assay having a corresponding calibration curve selected from a plurality of calibration curves, wherein a determination is made by the analyzer as to the suitability of at least one said calibration curve based on the read signal as compared to a threshold signal of the corresponding calibration curve at time points of the assay.

13. A method for scheduling a test in a clinical analyzer supporting an extended range, the method comprising the steps of:

initiating the test using a reaction mix;

measuring a signal strength from the reaction mix at a first time point subsequent to the initiation of the test selected from a plurality of time points subsequent to initiating the test;

determining analyte level using a first calibration curve corresponding to the first time point for measuring the signal strength, the first calibration curve being representative of signal strength corresponding to analyte values at the first time point and in which the measured signal strength is compared to a predetermined threshold signal strength value;

scheduling, if there is no corresponding calibration curve, a second time point subsequent to the initiation of the test for determining a second signal strength from the reaction mix; and determining analyte level using a second calibration curve corresponding to the second time point for measuring the signal strength.

14. The test scheduling method of claim 13 further comprising the step of scheduling multiple time points subsequent to the initiation of the test for measuring analyte levels using corresponding calibration curves.

15. The test scheduling method of claim 14, wherein a reported analyte level is a mean of measured analyte levels.

16. The test scheduling method of claim 15, wherein the reported analyte level is a weighted mean of measured analyte levels.

* * * * *

UNITED STATES PATENT AND TRADEMARK OFFICE
CERTIFICATE OF CORRECTION

PATENT NO. : 9,594,088 B2
APPLICATION NO. : 13/758562
DATED : March 14, 2017
INVENTOR(S) : Theodore J. DiMagno Page 1 of 1

It is certified that error appears in the above-identified patent and that said Letters Patent is hereby corrected as shown below:

On the Title Page

Item (73) Assignee
Change "Orth-Clinical Diagnostics, Inc.," to --Ortho-Clinical Diagnostics, Inc.,--

In the Claims

Column 17 Claim 2 Lines 6-7:
Change "curve from the plurality of calibration curves is satisfied at a first time point subsequent to initiation of the" to --curve from the plurality of calibration curves at a first time point subsequent to initiation of the--

Signed and Sealed this
Twenty-seventh Day of March, 2018

Andrei Iancu
*Director of the United States Patent and Trademark Office*